United States Patent
Sriraman et al.

(10) Patent No.: US 11,725,029 B2
(45) Date of Patent: Aug. 15, 2023

(54) EXPRESSION OF PNEUMOCOCCAL SURFACE PROTEIN A (PSPA)

(71) Applicant: Biological E Limited, Telangana (IN)

(72) Inventors: Rajan Sriraman, Hyderabad (IN); Ramesh Venkat Matur, Hyderabad (IN); Narender Dev Mantena, Hyderabad (IN); Mahima Datla, Telangana (IN); Swetha Kamireddy, Telangana (IN)

(73) Assignee: BIOLOGICAL E LIMITED

( * ) Notice: Subject to any disclaimer, the term of this patent is extended or adjusted under 35 U.S.C. 154(b) by 165 days.

(21) Appl. No.: 16/976,794

(22) PCT Filed: Mar. 1, 2019

(86) PCT No.: PCT/IB2019/051655
§ 371 (c)(1),
(2) Date: Aug. 31, 2020

(87) PCT Pub. No.: WO2019/167008
PCT Pub. Date: Sep. 6, 2019

(65) Prior Publication Data
US 2021/0009641 A1 Jan. 14, 2021

(30) Foreign Application Priority Data
Mar. 1, 2018 (IN) .............................. 201841007814

(51) Int. Cl.
| | | |
|---|---|---|
| C12Q 1/68 | (2018.01) | |
| C07K 14/315 | (2006.01) | |
| A61K 39/09 | (2006.01) | |
| C12N 15/77 | (2006.01) | |
| A61K 47/64 | (2017.01) | |
| A61K 39/116 | (2006.01) | |
| A61K 39/00 | (2006.01) | |

(52) U.S. Cl.
CPC ........ C07K 14/3156 (2013.01); A61K 39/092 (2013.01); A61K 39/116 (2013.01); A61K 47/646 (2017.08); C12N 15/77 (2013.01); *A61K 2039/6068* (2013.01)

(58) Field of Classification Search
None
See application file for complete search history.

(56) References Cited

FOREIGN PATENT DOCUMENTS

| | | |
|---|---|---|
| CN | 107674118 | 2/2018 |
| WO | WO 2009/158364 | 12/2009 |
| WO | WO 2010/141312 | 12/2010 |

OTHER PUBLICATIONS

English machine translation of Lichan et al. CN10764118. Feb. 9, 2018.*
Anonymous: "UPI00067DF074," Aug. 10, 2015 (Aug. 10, 2015), XP055599348, Retrieved from the Internet: URL:https://www.uniprot.org/uniparc/UPI00067DF074 [retrieved on Jun. 25, 2019].
Feldman et al., "Review: Current and new generation pneumococcal vaccines," J. Infect., 69(4):309-25 (publication date: Oct. 2014) Abstract only.
Figueredo et.al., "Production and purification of an untagged recombinant pneumococcal surface protein A (PspA4Pro) with high-purity and low endotoxin content," Appl Microbiol Biotechnol, 101(6):2305-2317 (publication date: Mar. 2017) Abstract only.
International Search Report and Written Opinion dated Jul. 18, 2019 for International Application No. PCT/IB2019/051655.
Masai et.al., "RepA and DnaA proteins are required for initiation of R1 plasmid replication in vitro and interact with the oriR sequence," Proc Natl Acad Sci USA, 84(14):4781-5 (publication date: Jul. 1987).
Nabors et.al., "Immunization of healthy adults with a single recombinant pneumococcal surface protein A (PspA) variant stimulates broadly cross-reactive antibodies to heterologous PspA molecules," Vaccine, 18(17):1743-54 (publication date: Mar. 6, 2020) Abstract only.
Nakano et.al., "Cloning of the Kanamycin Resistance Gene from a Kanamycin-Producing *Streptomyces* Species," J Bacteriol, 157(1):79-83 (publication date: Jan. 1984).
Nayak et.al., "A live recombinant avirulent oral *Salmonella* vaccine expressing pneumococcal surface protein A induces protective responses against *Streptococcus* pneumoniae," Infect. Immun., 66(8):3744-51 (publication date: Aug. 1988).

* cited by examiner

*Primary Examiner* — Jennifer E Graser
(74) *Attorney, Agent, or Firm* — Perkins Coie LLP

(57) ABSTRACT

The present invention relates to expression of Pneumococcal Surface Protein A (PspA). The invention represents an advancement in the field of genetic engineering and vaccine technology. The invention discloses expression vectors and recombinant host cells for expression of truncated PspA peptide. The invention also discloses vaccine compositions comprising the truncated peptides as carrier protein.

14 Claims, 14 Drawing Sheets

Specification includes a Sequence Listing.

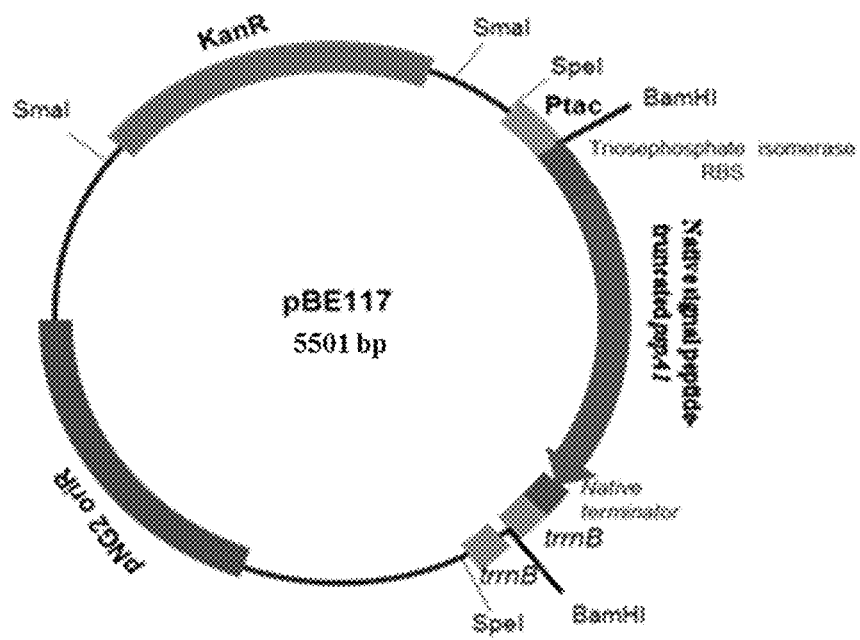
C
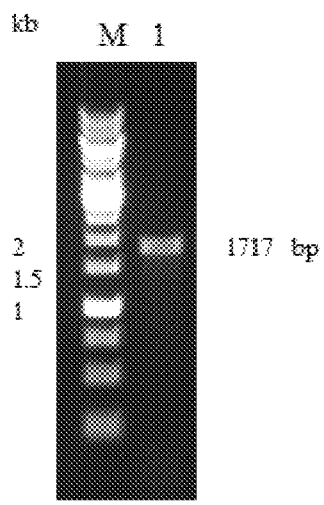
D
FIGURE 1 (cont.)

Protein sequence coverage: 31%

Underlined are the matched peptides

```
  1 ASSPTVVPAE DAPVANQSKA EKDYDAAPRQ AENAKKALED AKRAQEKYRD
 51 DQKITEERAE EEKKASQEQQ KAELQTQQKL EKYINEEDSE KRQMLQKDME
101 EAEEKQNEEQ AEFKKIEERV IESAEELEET EEKAEEAEAK EFELTEKVKE
151 AEEKVTEAEQ ELDAERAKEV ALQAKIAELE EEVERLETKL EETEEEDSED
201 TVEKGEEAPL QEELDAKQAK LSKLEELSDK IDELDAEIAK LEKDVEDFKN
251 SDEEYEALYL EAEEDLAAK KAELEKTEAD LKKAVEEPER PAPAPETPAP
301 EAPAEQPEPA PAPQPAPAPE PEPPAEQPEP EKTDQQQAEE QYAEESEEEY
351 HRLTQQPPK AEKPAPAPKP EQPAPGT
```

FIGURE 2

Lane 1: Load
Lane 2: FT
Lane 3: Wash
Lane 4: 40% of B
Lane 5: 80% of B Fr-1
Lane 6: 80% of B Fr-2
Lane 7: 0.5M Potassium phosphate Lane 1: Load
Lane 2: FT
Lane 3: Wash
Lane 4: F4
Lane 5: F5
Lane 6: F6
Lane 7: F7
Lane 8: F8
Lane 9: F4+F6+F7

Lane 1: 2.5 µg of PspA1
Lane 2: 5 µg of PspA1
Lane 3: 7.5 µg of PspA1
Lane 4: 10 µg of PspA1

(A) Type 3 Psp A Conjugate
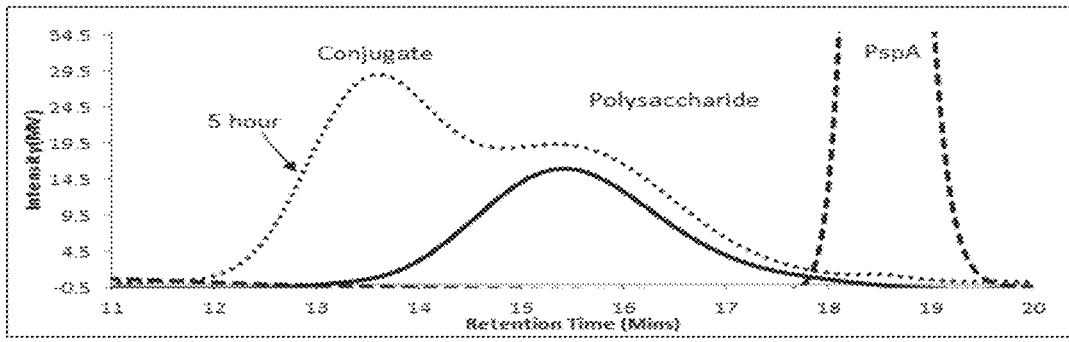
(B) Type 6A Psp A Conjugate
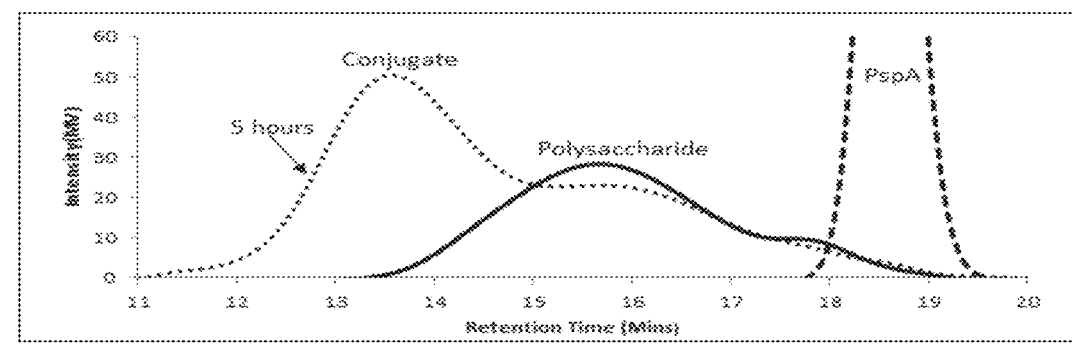
(C) Type 6B Psp A Conjugate
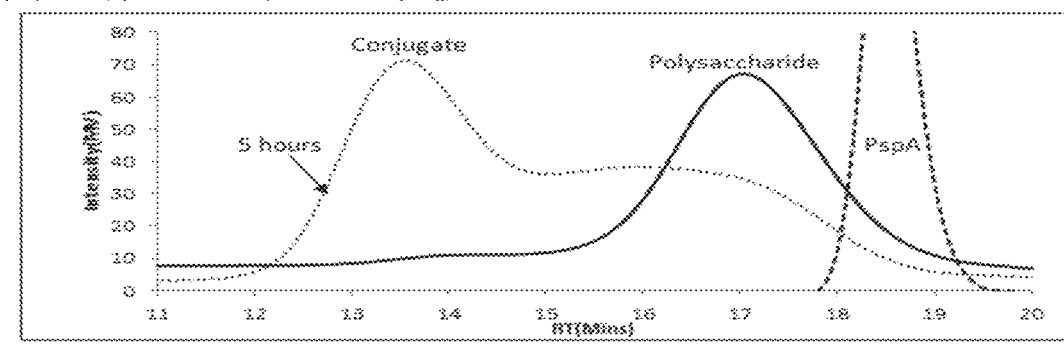
FIGURE 7

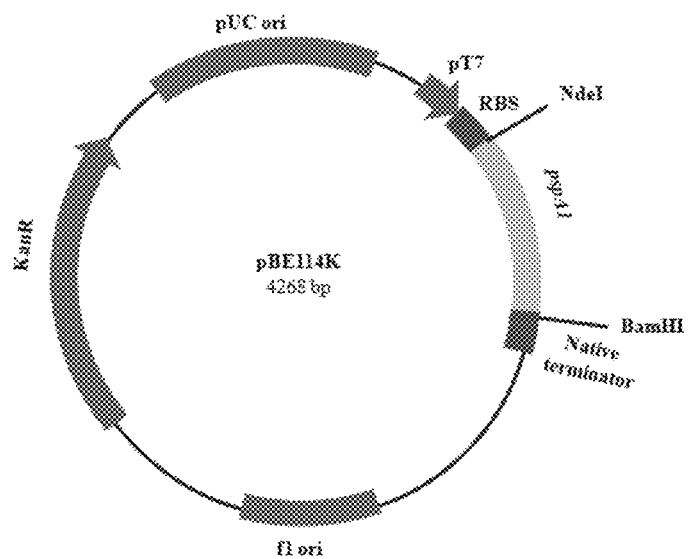
A
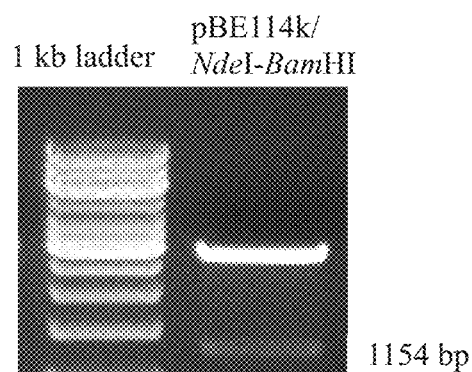
B
FIGURE 10

Lane 1: Load
Lane 2: FT
Lane 3: Wash
Lane 4: 50% of B
Lane 5,6,7 and 8: 80% of B
Lane 9: 0.5M Potassium phosphate Lane 1: Load
Lane 2: FT
Lane 3: Wash
Lane 4: Fr 4
Lane 5: Fr 5
Lane 6: Fr 6
Lane 7: Fr 7
Lane 8: Fr 8
Lane 9: Fr 9
Lane 10: Fr 10
Lane 11: Fr 11
Lane 12: Fr 12
Lane 13: Fr 13

Protein sequence coverage: 39%

Underlined are the matched peptides

```
  1 MNKKKMILTS LASVAILGAC FVASSPTVVR ASDAPVANQS KASKDYDAAK
 51 RDAENAKKAL EDAKRAQKKY KDDQKITEEK AEEEKKASQE QQKANLDYQQ
101 KLRKYINEKD SKKRSMLQKE MEEAEKRDKE KQAEFKKIRE KVIPSAEELT
151 ETRRRAEEAE AKEPELTKKV KEAEEKVTEA KQKLDAERAK EVALQAKIAE
201 LENEVHRLET KLKEIDESDS EDYVKEGLRA PLQSELDAKQ AKLSKLEELS
251 DKIDELDAKI AKLEKDVEDP KNSDGKYSAL YLEAAEKDLA AKKAELEKTE
301 ADLKKAVDEP EKPAPAPETP APEAPAEQPK PAPAPQPAPA PEPEKPAEQP
351 KPEKTDDQQA EEDYARRSEE EYNRLTQQQP PKAEKPAPAP KPEQPAPAPK
```

EXPRESSION OF PNEUMOCOCCAL SURFACE PROTEIN A (PSPA)

REFERENCE TO SEQUENCE LISTING SUBMITTED VIA EFS-WEB

This application includes an electronically submitted sequence listing in .txt format. The .txt file contains a sequence listing entitled "Sequence_Listing_ST25.txt" created on May 25, 2021 and is 36,735 bytes in size. The sequence listing contained in this .txt file is part of the specification and is hereby incorporated by reference herein in its entirety.

FIELD OF INVENTION

The present invention relates to high level expression of truncated Pneumococcal Surface Protein A1 (PspA1) in bacteria.

BACKGROUND

*Streptococcus pneumoniae* is an important cause of otitis media, meningitis, bacteremia and pneumonia, and a leading cause of fatal infections in the elderly and persons with underlying medical conditions. An attractive goal for streptococcal vaccination is to reduce carriage in the vaccinated populations and subsequently reduce the incidence of pneumococcal disease.

Pneumococcal polysaccharide vaccines marketed under the brand name Pneumovax23 is not effective in children under 2 years of age. The inefficacy of polysaccharide vaccines in this population has been attributed to the immaturity of the infant immune system in the expression of B cell receptors. Conjugation of polysaccharides (PS) to carrier proteins converts it from a T cell-independent antigen to a T cell-dependent antigen. As a T cell-dependent antigen, polysaccharides can raise a response with isotype switching, generation of memory cells and a boostable immunological response.

Membrane proteins exist within and span the membrane across which they serve to transport molecules or facilitate cell adhesion. The proteins may assist in the movement of substances by facilitated diffusion (i.e., passive transport) or active transport. The pneumococcal surface protein A (PspA) is a membrane protein and is another important virulence factor found attached to the cell wall of all *Streptococcus pneumoniae* strains.

The replacement of the universal carrier proteins, such as tetanus toxoid (TT) or CRM197, by a pneumococcal protein in particular PspA1 or a fragment thereof, besides broadening the vaccine coverage, would also prevent the impairment of immune responses caused by the excessive use of the same carrier proteins in conjugate vaccines. An expression plasmid is engineered to contain regulatory sequences that act as enhancer and promoter regions and lead to efficient transcription of the gene carried on the expression vector. The goal of a well-designed expression vector is efficient production of protein, and this may be achieved by synthesizing significant amount of stable messenger RNA. It is possible to design an expression vector that exert a tight control of the expression, and the protein is only produced in high quantity when necessary through the use of suitable expression conditions. In absence of the tight control of the gene expression, the protein may also be expressed constitutively.

*Corynebacterium glutamicum* is a gram positive fermentative bacterium that is widely used in the production of mono-sodium glutamate, in high amounts. Owing to its stable genetic characteristics and lack of any endotoxin, *Corynebacterium glutamicum* is classified as GRAS organism (generally regarded safe). The bacterium is not known to secrete any extracellular proteases, hence it becomes an attractive platform for producing heterologous proteins into the medium. This can be achieved using an expression plasmid construct that can synthesize the recombinant protein in high amounts.

EP2310502 B1 discloses the use of $P_{tac}$ promoter in a construct wherein an *Escherichia coli* strain containing IPTG inducible ftsZ and minCDE deletion mutation were grown in LB medium.

Nokano et. al., *J Bacteriol.* 1984 January; 157(1):79-83 discloses use of kanamycin resistance gene in the plasmid construct in order to make the transformed strain which acquire the property of being resistant to kanamycin.

Masai et.al., *Proc Natl Acad Sci USA.* 1987 July; 84(14): 4781-5 discloses RepA protein for initiation of R1 plasmid replication and interact with oriR sequence.

Nayak et.al., Infect. Immun.-1998-Nayak-3744-51 discloses a live oral recombinant *Salmonella* vaccine strain expressing pneumococcal surface protein A (PspA).

Nabors et.al., *Vaccine* 18 (2000) 1743-54 discloses the expression of recombinant truncated PspA as cytoplasmic protein in *Escherichia coli*.

Figueredo et.al., Appl Microbiol Biotechnol (2017) 101: 2305-2317 discloses Production and purification of an untagged recombinant pneumococcal surface protein A (PspA4Pro).

The above-mentioned references either disclose the genetic elements of the expression vector or expression of pneumococcal surface protein A in *Escherichia coli* and *Salmonella*.

The inventors have identified immunogenic fragments of Pneumococcal Surface Protein. Thereafter, the inventors have made extensive efforts to develop expression constructs capable of stable and constitutive or inducible expression of the truncated pneumococcal surface protein A1 (PspA1) in bacteria at high level.

Therefore, the present invention contemplates to overcome the challenges of the prior art by preparing expression vectors and recombinant host cells for expression of truncated pneumococcal surface proteins. Further, inventors have prepared vaccine compositions comprising the truncated proteins as carrier proteins.

OBJECTIVE

The main objective of the present invention is to provide an expression construct for the high-level expression of truncated pneumococcal surface protein A1 (PspA1) in bacteria.

Another objective of the present invention is to provide an expression construct capable of stably and constitutively or inducibly expressing a high level of truncated pneumococcal surface protein A1 (PspA1) in bacteria.

SUMMARY

The present invention provides an expression construct capable of high level expression of truncated pneumococcal surface protein A1 (PspA1) as set forth in SEQ ID NO: 3 and 4.

The present invention provides an expression construct comprising a gene, which encodes for truncated pspA1, as set forth in SEQ ID NO: 5 and 6.

The present invention provides an expression construct for the high-level expression of truncated PspA1 (Pneumococcal Surface Protein A1) as set forth in SEQ ID NO: 3 or 4, in bacteria comprising:
a) gene encoding truncated pspA1 as set forth in SEQ ID NO: 5 or 6,
b) origin of replication,
c) Antibiotic resistance gene,
d) A promoter and
e) ribosomal binding site.

The present invention is also directed to a method for high level expression of truncated PspA1 (Pneumococcal Surface Protein A1) which comprises culturing of bacteria transformed with an expression construct and thereby purifying the expressed protein.

BRIEF DESCRIPTION OF THE DRAWINGS

FIG. 2 (SEQ ID NO: 28): Protein sequence coverage of truncated PspA1 in a peptide fingerprint analysis.

FIG. 7: SEC-HPLC chromatogram for conjugation reaction kinetics of pneumococcal polysaccharide Serotype 3 (A), 6A (B) and 6B (C).

FIG. 10: Panel A shows the diagrammatic representation of pBE114k. Panel B shows the confirmation of pBE114k by restriction digest.

FIG. 13 (SEQ ID NO: 29): Protein coverage of PspA1 by MALDI.

DETAILED DESCRIPTION

Figure 1:
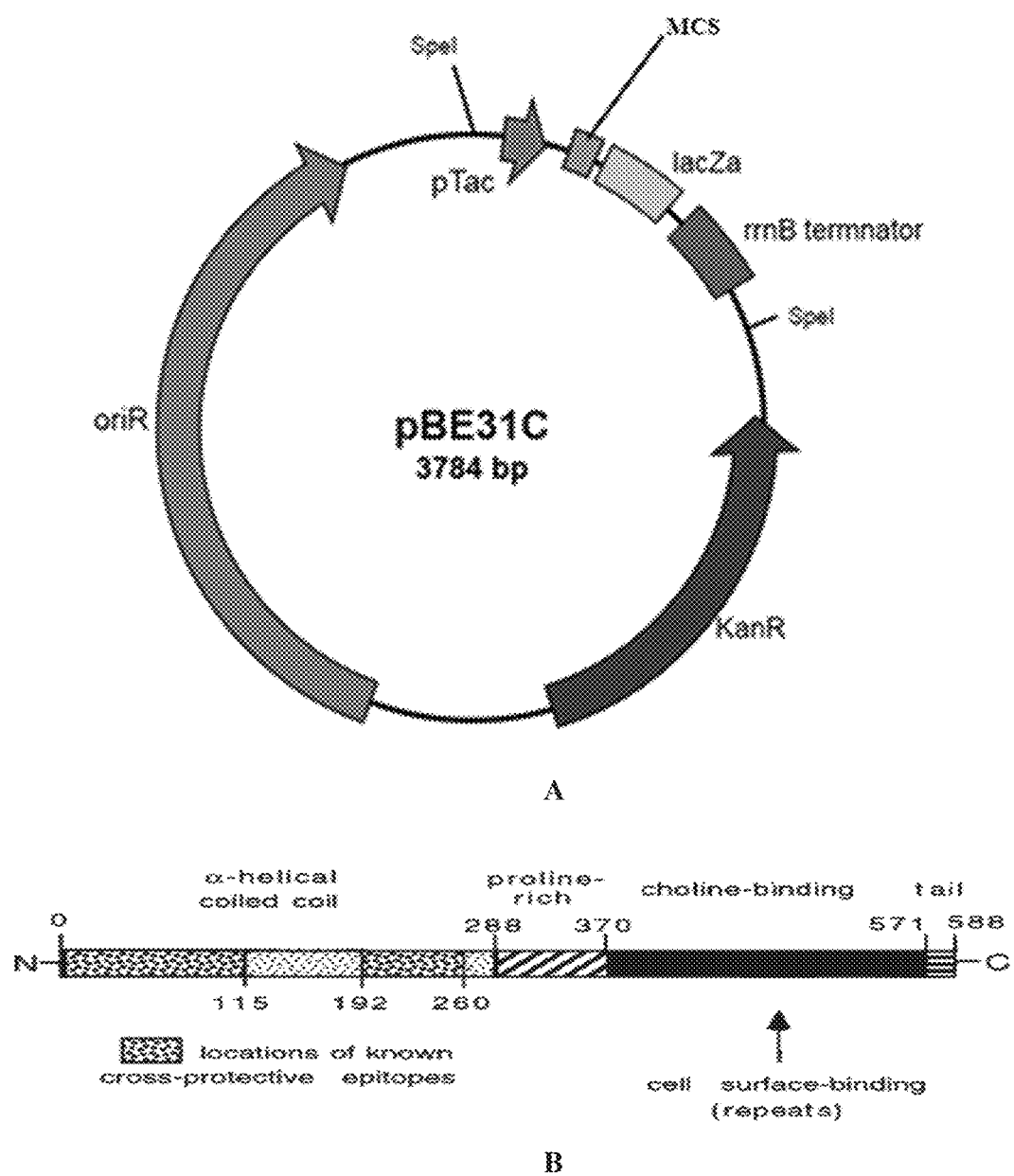
FIG. 1: Panel A shows the diagrammatic representation of pBE31C. Panel B shows sschematic presentation of the domains of pspA delineated from the deduced amino acid sequence of Rx1 pspA1. Panel C shows the diagrammatic representation of pBE117. Panel D shows the PCR amplicon containing RBS, native signal peptide, truncated pspA1, native terminator and trrnB.

The term PspA1 refers to Pneumococcal Surface Protein A1 from *Streptococcus pneumonia*.

The present invention relates to high level expression of truncated PspA1 (Pneumococcal Surface Protein A1) in bacteria. The bacteria suitable for high level expression of pspA1 is *Corynebacterium glutamicum* and *Escherichia coli*.

In an embodiment, the present invention relates to high level expression of truncated PspA1 (Pneumococcal Surface Protein A1) as set forth in SEQ ID NO: 3 in *Corynebacterium glutamicum*.

In another embodiment, the present invention relates to high level expression of truncated PspA1 (Pneumococcal Surface Protein A1) as set forth in SEQ ID NO: 4 in *Escherichia coli*.

The present invention provides an expression construct capable of high level expression of surface protein as set forth in SEQ ID NO: 3.

The present invention also provides an expression construct capable of high level expression of surface protein as set forth in SEQ ID NO: 4.

In another embodiment, the present invention relates to an expression construct for high level expression of truncated PspA1 (Pneumococcal Surface Protein A1) as set forth in SEQ ID NO: 3 in *Corynebacterium glutamicum*.

In yet another embodiment, the present invention relates to an expression construct for high level expression of truncated PspA1 (Pneumococcal Surface Protein A1) as set forth in SEQ ID NO: 4 in *Escherichia coli*.

The present invention relates to an expression construct which is used for the high-level expression of truncated PspA1 in *Corynebacterium glutamicum* comprising:
i. ori R origin of replication,
ii. Kanamycin resistance gene,
iii. $P_{tac}$ promoter,
iv. Gene of interest coding for a truncated pspA1 (SEQ ID NO: 5).

The present invention also relates to an expression construct which is used for the high-level expression of truncated PspA1 in *Escherichia coli* comprising:
i. pUC origin of replication
ii. Kanamycin resistance gene
iii. $P_{T7}$ promoter
iv. Gene of interest coding for a truncated pspA1 (SEQ ID NO: 6).

In an embodiment, the expression construct for high level expression of truncated pspA1 further comprises ribosomal binding site (RBS). RBS is included in the forward primer and a short stretch of DNA containing native terminators are included in the reverse primer used for further amplification of truncated pspA1. The RBS (Ribosomal Binding Site) is Triose phosphate isomerase in the expression construct for the expression of truncated PspA1 in *Corynebacterium glutamicum*.

In an embodiment of the present invention, the expression construct comprises PspA1 signal peptide coding region (native), truncated pspA1, $P_{tat}$ promoter and Ribosomal binding site (RBS) of triose phosphate isomerase gene.

In a preferred embodiment, the present invention provides an expression construct for high level expression of truncated PspA1 (SEQ ID NO: 3), in *Corynebacterium glutamicum* which comprises:
a. gene encoding truncated pspA1 (SEQ ID NO: 5),
b. ori R origin of replication (SEQ ID NO: 12),
c. kanamycin resistance gene (SEQ ID NO: 1),
d. $P_{tac}$ promoter (SEQ ID NO: 2) and
e. triose phosphate isomerase ribosomal binding site.

In another preferred embodiment, the present invention provides an expression construct for high level expression of truncated PspA1 (SEQ ID NO: 4), in *Escherichia coli* which comprises:

a) gene encoding truncated pspA1 (SEQ ID NO: 6),
b) pUC origin of replication,
c) kanamycin resistance gene (SEQ ID NO: 1),
d) PT7 promoter (SEQ ID NO: 11), and
e) ribosomal binding site.

The pneumococcal surface protein A (PspA) is a membrane protein and is an important virulence factor found attached to the cell wall of all *Streptococcus pneumoniae* strains and is a promising component as has been shown to be highly immunogenic.

In a particular embodiment of the present invention, truncated PspA1 is used as a carrier protein. Carrier proteins, employed in the conjugate vaccines, are preferably proteins that are non-toxic and non-reactogenic and obtainable in large amount and purity. A carrier protein can be conjugated to capsular polysaccharide isolated from pathogenic bacteria to enhance immunogenicity of the polysaccharide. Carrier proteins should be amenable to standard chemical conjugation procedures.

The truncated PspA1 in *Corynebacterium glutamicum* is secreted into the extracellular medium. The secretion into the extracellular medium aids in efficient purification.

The present invention relates to high level expression of truncated PspA1 in *Corynebacterium glutamicum* wherein the N-terminal region along with proline rich region of truncated pspA1 gene was amplified from 23F capsular serotype of *Streptococcus pneumoniae*, together with the upstream region.

In an embodiment of the present invention, the expression construct comprises truncated pspA1, $P_{tac}$ promoter and Ribosomal binding site (RBS) of triose phosphate isomerase gene.

In an embodiment of the present invention, the expression construct comprises truncated pspA1, PT7 promoter and Ribosomal binding site (RBS).

The expression construct is electroporated into *Corynebacterium glutamicum* and selected on LB plates with kanamycin as selectable marker.

$P_{tac}$ is a strong hybrid promoter composed of the −35 region of the trp promoter and the −10 region of the lacUV5 promoter/operator.

pspA sequences were obtained from GenBank and aligned from the protein database. Primers were designed to specifically amplify native signal peptide coding region, N-terminal region along with the proline rich region of pspA genes belonging to families 1 & 2. The required regions of pspA1 and pspA2 were amplified from the available *Streptococcus pneumoniae* clinical isolates. MHC peptide analysis showed that pspA1 is comparatively more immunogenic than pspA2.

Amino acid sequence encoding truncated PspA1 expressed and produced in *Corynebacterium glutamicum* is set forth in SEQ ID NO: 3 having an intact mass observed to be 35452 Daltons.

Amino acid sequence encoding truncated PspA1 expressed and produced in *Escherichia coli* is set forth in SEQ ID NO: 4 having an intact mass observed to be 41966 Daltons.

DNA sequence encoding truncated pspA1 expressed in *Corynebacterium glutamicum* and *Escherichia coli* are set forth in SEQ ID NO: 5 and SEQ ID NO 6 respectively.

*Corynebacterium glutamicum* (previously known as *Micrococcus glutamicus*) used for expressing the truncated pspA1 is a GRAS organism Gram-positive, rod-shaped bacteria. *Corynebacterium glutamicum* is a GRAS organism. The whole genome sequence of *Corynebacterium glutamicum* ATCC 13032 is available which can be grown to higher cell densities and is also genetically stable owing to the lack of a recombination repair system. It has limited restriction-modification system. It shows no autolysis and can maintain metabolic activity under growth-arrested conditions. It has low protease activity favoring recombinant protein production. Its plasticity of metabolism and strong secondary metabolism properties, capacity to utilize broad spectrum of carbon sources (pentoses, hexoses, and alternative carbon sources), stress-tolerance to carbon sources make it a promising host for heterologous protein production. These physiological properties make *Corynebacterium glutamicum* accessible to manipulation and cultivation in robust industrial conditions, thus making it a successful industrial workhorse. Heterologous expression of proteins like α-Amylase, endoglucanase, endoxylanase, GFP, Xylanse etc., was reported in *Corynebacterium glutamicum*.

In an embodiment of the present invention, the yield of truncated PspA1 is about 500 mg/L, about 400 mg/L, about 300 mg/L, about 250 mg/L, about 220 mg/L, about 200 mg/L, about 180 mg/L, about 160 mg/L, about 150 mg/L, about 120 mg/L, about 100 mg/L.

In yet another embodiment, the present invention provides a pneumococcal conjugate vaccine comprising at least one polysaccharides from *Streptococcus pneumoniae* serotypes selected from 1, 2, 3, 4, 5, 6A, 6B, 6C, 6D, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, conjugated with truncated pspA1 of the present invention or combination of truncated PspA1 and other carrier proteins such as CRM197, tetanus toxoid, pertussis toxoid; PsaA and the like.

In yet another embodiment, the present invention provides multivalent pneumococcal vaccine composition selected from 10 valent, 14 valent, 15 valent, 17 valent, 18 valent, 19 valent, 20 valent, 22 valent, 23 valent, 24 valent or 25 valent comprising polysaccharides from *Streptococcus pneumoniae* serotypes selected from 1, 2, 3, 4, 5, 6A, 6B, 6C, 6D, 7F, 8, 9N, 9V, 10A, 11A, 12F, 14, 15A, 15B, 15C, 16F, 17F, 18C, 19F, 19A, 20A, 20B, 22F, 23A, 23B, 23F, 24B, 24F, 31, 33F, 34, 35B, 35F, 38, 39 and 45, conjugated with truncated pspA1 of the present invention or combination of truncated PspA1 and other carrier proteins such as CRM197, tetanus toxoid, pertussis toxoid; psaA and the like.

In a preferred embodiment, the present invention provides a multivalent conjugate vaccine comprising at least three polysaccharides from *Streptococcus pneumoniae* serotypes 3, 6A and 6B conjugated to truncated PspA1 of the present invention.

In an embodiment of the present invention provides a conjugate vaccine comprising polysaccharides from *Streptococcus pneumoniae* serotypes 3, 6A and 6B conjugated to truncated PspA1 of the present invention and *Streptococcus pneumoniae* serotypes 1, 4, 5, 7F, 9V, 14, 18C, 19A, 19F, 22F, 23F and 33F conjugated to CRM197.

The present invention provides formulations containing either 2.2 μg or 4.4 μg of each of the pneumococcal polysaccharides from serotypes 3, 6A and 6B each conjugated to truncated PspA1 of the present invention and about 2.2 μg each of pneumococcal polysaccharides from serotypes 1, 4, 5, 7F, 9V, 14, 18C, 19A, 19F, 22F, 23F and 33F each conjugated to $CRM_{197}$.

In another embodiment, the present invention provides a pneumococcal vaccine composition as a single 0.5 mL dose, the single dose comprising about 2.2 to 4.4 μg of one or more pneumococcal polysaccharides; about 1 μg to about 50 μg of truncated PspA1 of the present invention conjugated to each of the one or more pneumococcal polysaccharides; about 0.2 mg to about 1 mg of aluminum phosphate adjuvant; and an excipient.

In another embodiment, the present invention provides a pneumococcal vaccine composition as a single 0.5 mL dose, the single dose comprising about 2.2 to 4.4 µg of one or more pneumococcal polysaccharides; about 1 µg to about 30 µg of truncated PspA1 of the present invention conjugated to each of the one or more pneumococcal polysaccharides; about 1 µg to about 30 µg of CRM197 conjugated to each of the one or more pneumococcal polysaccharides; about 0.2 mg to about 1 mg of aluminum phosphate adjuvant; and an excipient.

In another embodiment, the present invention also provides a vaccine for the prevention of invasive disease caused by Streptococcus pneumoniae, by administering the conjugated vaccine prepared by conjugating the truncated PspA1 of the present invention with pneumococcal polysaccharides.

EXAMPLES

The following examples are provided to illustrate the invention and are merely for illustrative purpose only and should not be construed to limit the scope of the invention.

Example 1: Recombinant Expression of Truncated PspA1 in Corynebacterium glutamicum
Construction of pBE31C A small stably replicating broad host range plasmid pBE30 was generated using synthetic plasmid having 2.692 Kb pNG2 oriR sequence. Using this plasmid DNA as template, a 1.8 Kb oriR region was amplified using the primers pEP-F1 (5'-GCG CGG ACT AGT AGA TCT ATG GTA AAT CTG CGC AGA CAG-3')(SEQ ID NO: 16) and pEP-R1 (5'-GCG CGG ACT AGT GAA TTC GGT GAG GTT ATG GCG-3') (SEQ ID NO: 17).

Simultaneously, 1.033Kb kanR sequence was amplified using pUC4-KIXX template DNA and Kan-F2 (5'-AAG GTC CCG GGA TGG CGA TAG CTA GAC TGG GCG GT-3') (SEQ ID NO: 18) and Kan-R2 (5'-AAG GTC CCG GGG GTT GGG CGT CGC TTG GTC GG-3') (SEQ ID NO: 19) primers. Both kanR gene amplicon and oriR amplicon were blunt end ligated to create pBE30 vector. Further, a 0.851 Kb expression cassette containing a tandem of tac lac UV5 promoter, multiple cloning site, lacZa component and TrmB terminator sequence was amplified using the $P_{tac}$-F1 (5'-GG AGC ACT AGT CTG AAA TGA GCT GTT GAC AAT TAA TC-3') (SEQ ID NO: 20) and $P_{tac}$-R1 (5'-GG AGC ACT AGT TTT AAA CAT GAG CGG ATA CAT ATT TGA A-3') (SEQ ID NO: 21) primers each appending SpeI restriction site. The template DNA used for the amplification of expression cassette is pMMB206 (ATCC 37808). Later the expression cassette was cloned into the unique SpeI site designed in the pBE30 plasmid. The plasmid thus obtained is designated as pBE31C (FIG. 1A; SEQ ID NO: 14).

Construction of pBE117

Truncated pspA1gene (N terminal region along with proline rich region FIG. 1B) was amplified from 23F capsular serotype of Streptococcus pneumoniae, together with the upstream region. This was cloned in a TA vector (pTZ57R/T procured from Fermentas) using primers PSPAF1 FP (5'ATG AAT AAG AAA AAA ATG ATT TTA ACA AGT CTA GCC 3') (SEQ ID NO: 22) and PSPAF1 RP (5'CGA GAG AGA TCT AAA TTA AAA TGT CAA ATG TTC TTA ACA TGC TTT AAT TTT TAT TTT GGT GC 3') (SEQ ID NO: 23) and sequence verified. This was designated as pTZ-pspA1. Native terminator sequence was included in the reverse primer PSPAF1 RP. The clade defining regions were mapped in the obtained truncated pspA1 sequence to confirm that it belongs to family 1 of PspA proteins.

To express truncated pspA1 in Corynebacterium glutamicum, $P_{tac}$ promoter (SEQ ID NO: 2) and Ribosomal binding site (RBS) of triose phosphate isomerase gene (SEQ ID NO: 7) belonging to Corynebacterium, were chosen. pspA1 gene along with the entire cassette including RBS, native signal peptide (SEQ ID NO: 8), truncated pspA1gene, native terminator (SEQ ID NO: 10) was amplified using primers—SDTICGR0949_FP5 (5' GAG CGA TGG ATC CTA GAA AGG TGT GTT TCA CCC ATG AAT AAG AAA AA 3') (SEQ ID NO: 24) and PSPA2_2RP (5' TCA AAT GTT CTT AAC ATG CTT TAA TTT TTA TGG TGC AGG AGC TGG TTG 3') (SEQ ID NO: 25) and pTZ-pspA1 as template. RBS was included in the forward primer SDTICGR0949_FP5. rrnB terminator (SEQ ID NO: 13) region was amplified from pBE31C available in-house and ligated to gene encoding for truncated pspA1 using Splicing by Overlap Extension (SOE) PCR. rrnB gene was amplified using TER FP2 (5' ATG TTA AGA ACA TTT GAC ATT TTA ATT TCG GCA CTG GCC GTC GTT 3') (SEQ ID NO: 26) and TER_RP3 (5'GCG ATA TGG ATC CCA TGA GCG GAT ACA 3') (SEQ ID NO: 27). PSPA2_2RP and TER FP2 were designed such that there is an overlap of 17 bases. Both the amplicons pspA1 and rrnB were added in the molar ratio of 1:1 and used as template for SOE PCR with the primers SDTICGR0949_FP5 (5' GAG CGA TGG ATC CTA GAA AGG TGT GTT TCA CCC ATG AAT AAG AAA AA 3') (SEQ ID NO: 24) and TER_RP3 (5'GCG ATA TGG ATC CCA TGA GCG GAT ACA 3') (SEQ ID NO: 27). Subsequently, the entire amplicon including RBS, native signal peptide (SEQ ID NO: 8), truncated pspA1 gene, native terminator (SEQ ID NO: 10), rrnB terminator was digested with the restriction enzyme appended in the forward (SDTICGR0949_FP5) and reverse primers (TER_RP3) and cloned in an expression vector pBE31C made for Corynebacterium. The resulted clone was designated as an expression construct pBE117 (FIG. 1C; SEQ ID NO: 15). The expression vector along-with truncated pspA1 hereinafter is referred to as expression construct. The orientation of the insert (FIG. 1D) was confirmed by PCR analysis. The sequence of truncated pspA1gene along with its expression cassette was confirmed by DNA sequencing.

Expression of Truncated PspA1

The expression construct was electroporated into Corynebacterium glutamicum ATCC 13032 and selected on LB plates with kanamycin as selectable marker. Twenty recombinant Corynebacterium glutamicum colonies were picked and analysed by PCR. Five colonies were chosen for constitutive expression of truncated pspA1. The recombinant colonies along with Corynebacterium glutamicum ATCC 13032 (as negative control) were inoculated into 10 ml Terrific Broth with 25 µg/ml final concentration of kanamycin and incubated at 35° C. with shaking at 200 rpm. After 16 h, secondary inoculation was done in 10 ml of the same medium described above, such that the final OD is 0.1. The cultures were incubated at 35° C. with shaking at 200 rpm for 18-20h. After 18 h, the culture supernatants were checked for the expression of truncated pspA1. 30 µl of the supernatant was loaded onto 12% SD S-PAGE and analysed for truncated pspA1 expression. A prominent band was seen around 45 kDa.

Western analysis using N terminal epitope specific pspA polyclonal antibody (SantaCruz) confirmed the expression of truncated pspA1. The expression analysis of recombinant clone 5 was scaled up to 500 ml and the expression of truncated pspA1 was confirmed at least 3 times. Truncated pspA1 was initially purified from shake flask experiments using CHT type 1 and Capto Q impress to nearly 99% purity. Later, after confirming the consistent expression of truncated PspA1 in *C. glutamicum*, the expression was scaled up to 1.5 L.

Purification and Validation of Truncated PspA1

The 800 ml of culture supernatant containing truncated PspA1 from 1.6 L (0.66 mg/ml), obtained from upstream was dialysed through 10 kDa and concentrated to 260 ml (1.92 mg/ml). 70 ml of this dialysed concentrate was subjected to purification using CHT type 1 and Capto Q impress. The final recovery of truncated pspA1 was 162 mg/L.

Figure 3:
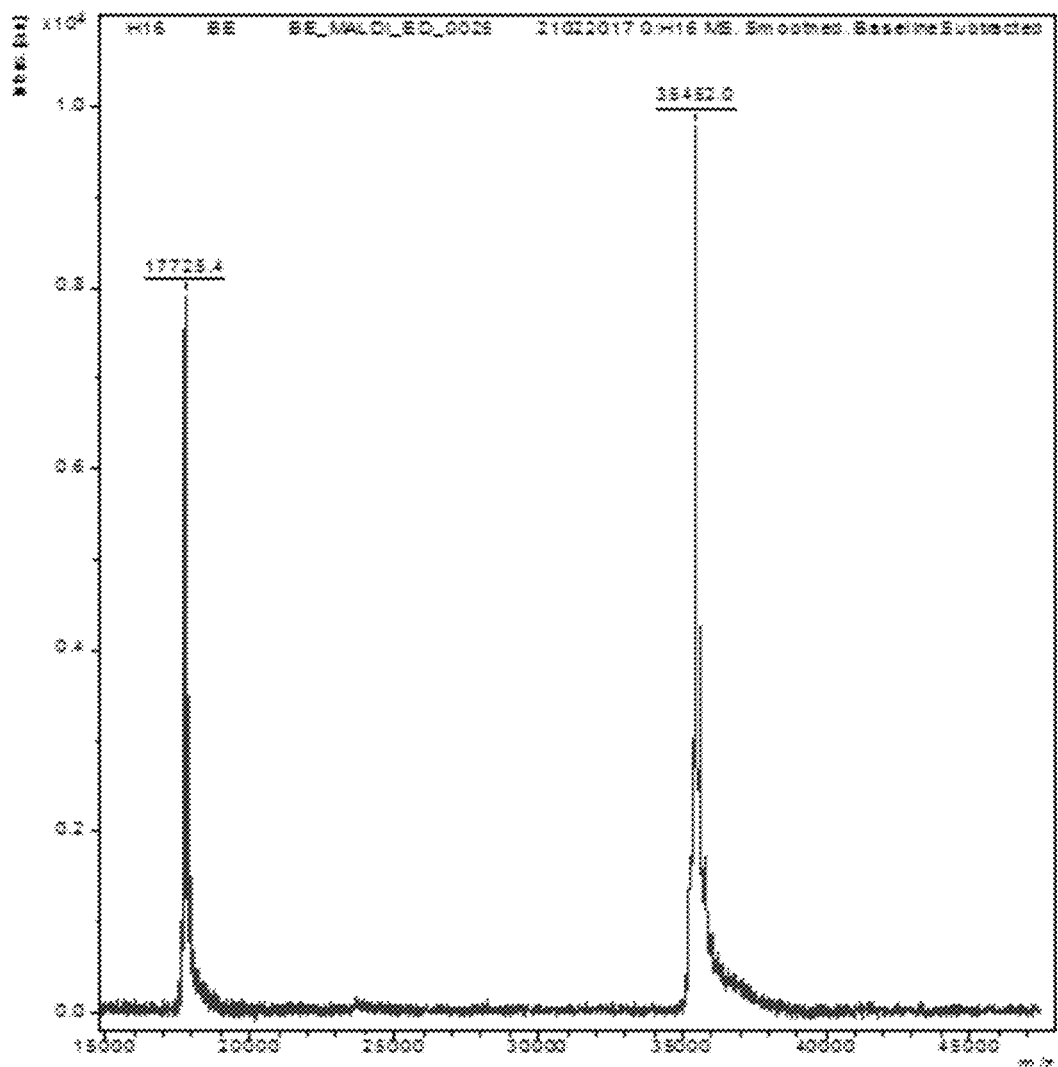
FIG. 3: Intact mass analysis of the truncated PspA1 expressed in *Corynebacterium glutamicum*.

MALDI MS/MS analysis of the gel plug containing purified truncated PspA1 from SDS-PAGE gave a clear hit score of 233 with Pneumococcal surface protein A. 31% (FIG. 2) sequence coverage was shown with the PspA protein with NCBI protein id ABY67187.1. The intact molecular weight analysis showed the molecular weight of the truncated pspA1 expressed is 35.4 kDa. This mass matches with the theoretical molecular weight of truncated pspA1. The peak at 17725.4 is a peak of molecule having a charge of 2, hence in the m/z the peak appears at half the intact mass of the truncated pspA1. (FIG. 3)

Example 2: Production of Truncated PspA1

*Corynebacterium glutamicum* ATCC 13032 harbouring the expression construct comprising truncated pspA1 (hereinafter referred as pspA1) gene was revived from a source bank in LB media. This was used to inoculate a fermenter vessel (5L; CSTR). The parameters that were monitored during the production process were—pH, DO, Temperature ($\Delta$T), Carbon source, Metabolites. Process automation technology (PAT) based feeding strategy was adopted for carrying out Short Fed-Batch of truncated PspA1 fermentation. There was no induction-based control of the product (truncated PspA1) as this was growth associated product. The harvest OD was approximately 90 ($OD_{600nm}$) at the time of harvest in a semi-synthetic media. The cells were harvested and washed with PBS, prior to cell disruption in a French Press.

Purification of Truncated PspA1

Figure 4:
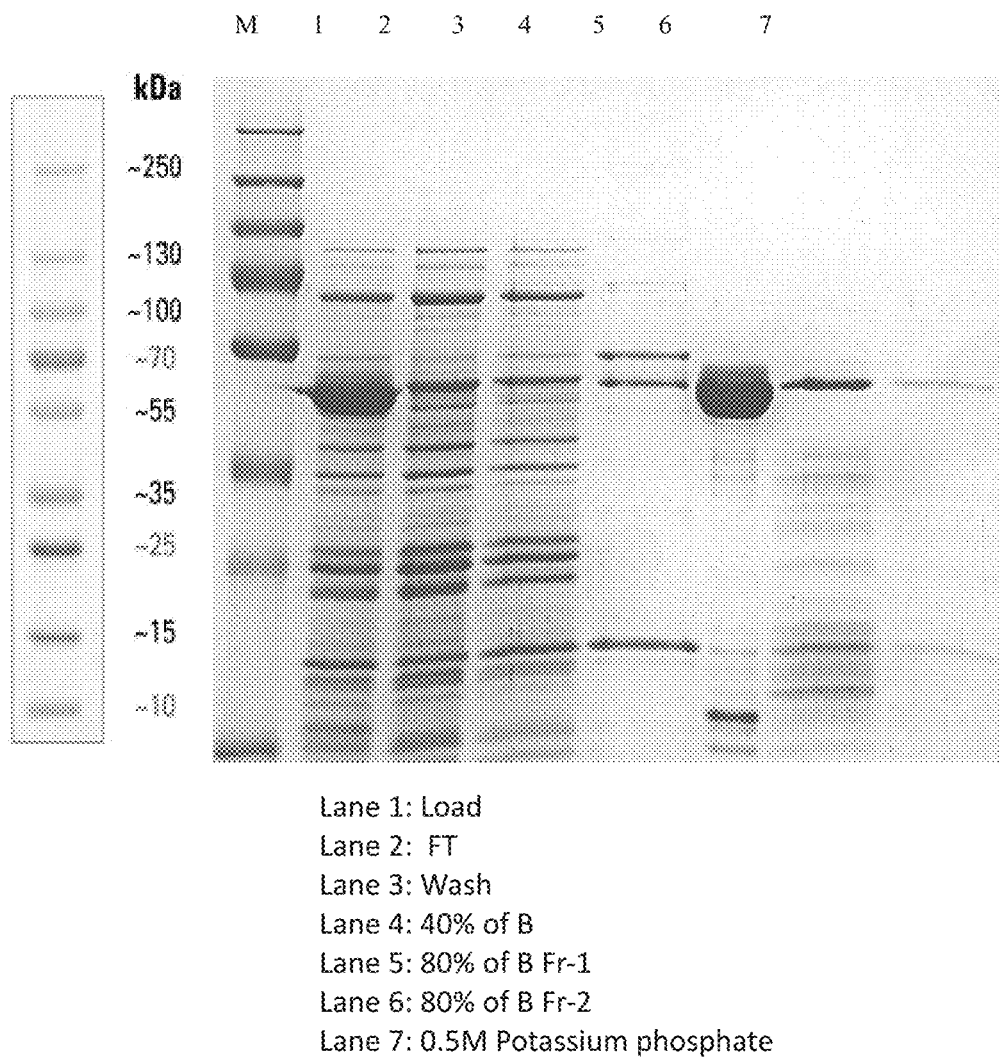
FIG. 4: Truncated PspA1 eluted from ceramic hydroxyapatite (CHT-II) column.

16.2 L spent medium, with a total protein concentration of 0.8 mg/mL, was collected from 20 L fermentation batch. 16.2 L spent media was concentrated to 2.6 L (3.6 mg/mL) by using 10 kDa 0.5 $m^2$ cassette followed by Dia filtration against 20 mM Potassium phosphate pH-6.8, cond 3.2 ms/cm. This 2.6 L was split into two lots i.e Lot 1 with 1.4 L and Lot 2 with 1.2 L and proceeded to further purification. 500 ml of CHT I resin was packed in Hi Scale 50/40 column. Resin was washed with sterile distilled water followed by equilibration with 8 column volumes (CV) of 20 mM Potassium Phosphate pH-6.8 (Buffer A). 1400 mL (3.6 mg/mL) of the spent media concentrate (Lot 1) was loaded onto the column and flow through was collected. Column was washed with 5 column volumes of Buffer A. PspA1 was eluted with Step gradient using 250 mM Potassium Phosphate pH-6.8 (Buffer B). The step gradient involved 5 CVs of Step-40% B, 5 CVs of Step-80% B and 3 CVs of 0.5M Potassium Phosphate buffer. The flow rate was maintained at 80 mL/min for the entire run. PspA1 was collected in fraction 1 of Step-80% B with a fraction volume of 1250 mL. (FIG. 4)

Figure 5:
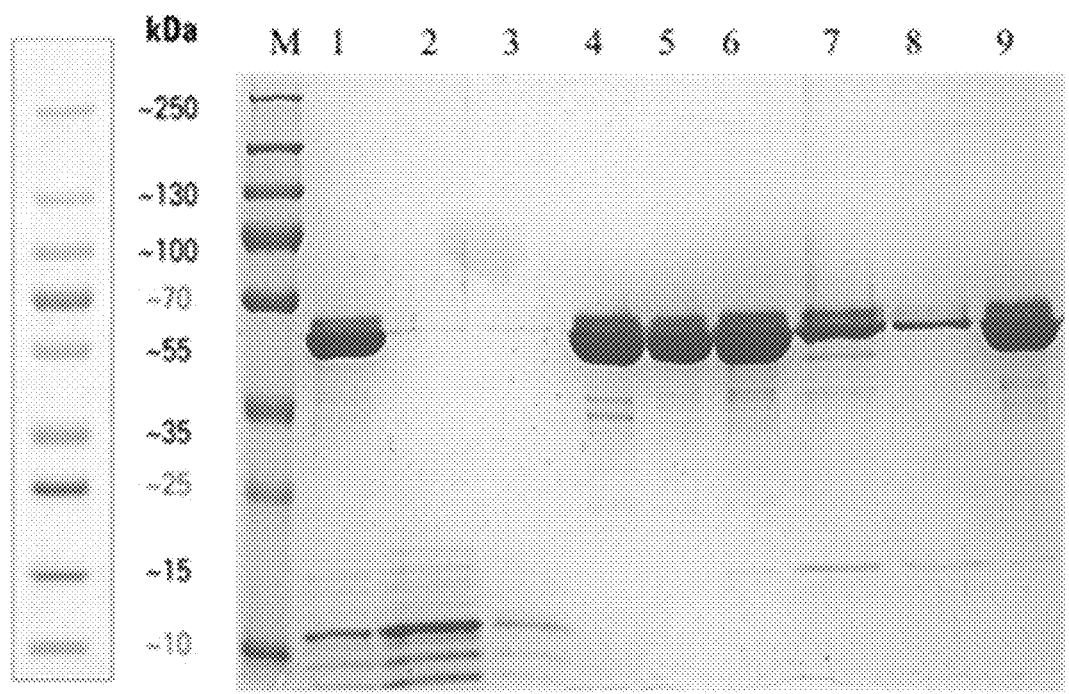
FIG. 5: Truncated PspA1 eluted from anion exchange column.

Capto Q Impress was used as a second chromatography step in PspA1 purification. 250 ml of Capto Q Impress resin was packed in XK 50/20 column. Resin was washed with sterile distilled water followed by equilibration with 5 column volumes (CV) of 20 mM Potassium Phosphate and 100 mM NaCl, pH-6.8 (Buffer A). 1250 mL of CHT I fraction was diluted to 2300 mL with 20 mM Potassium Phosphate, pH-6.8, loaded onto the column and flow through was collected. Column was washed with 5 column volumes of Buffer A. PspA1 was eluted using 12 CVs of Buffer B (20 mM Potassium Phosphate with 1 M NaCl, pH-6.2) in a linear gradient of 0 to 40% B and a final step of 3 CVs of 100% B. Each fraction of 250 mL was collected. The flow rate was maintained at 40 mL/min. PspA1 was collected in linear gradient of 40% B with pooled fraction volume of 1250 mL. (FIG. 5)

Figure 6:
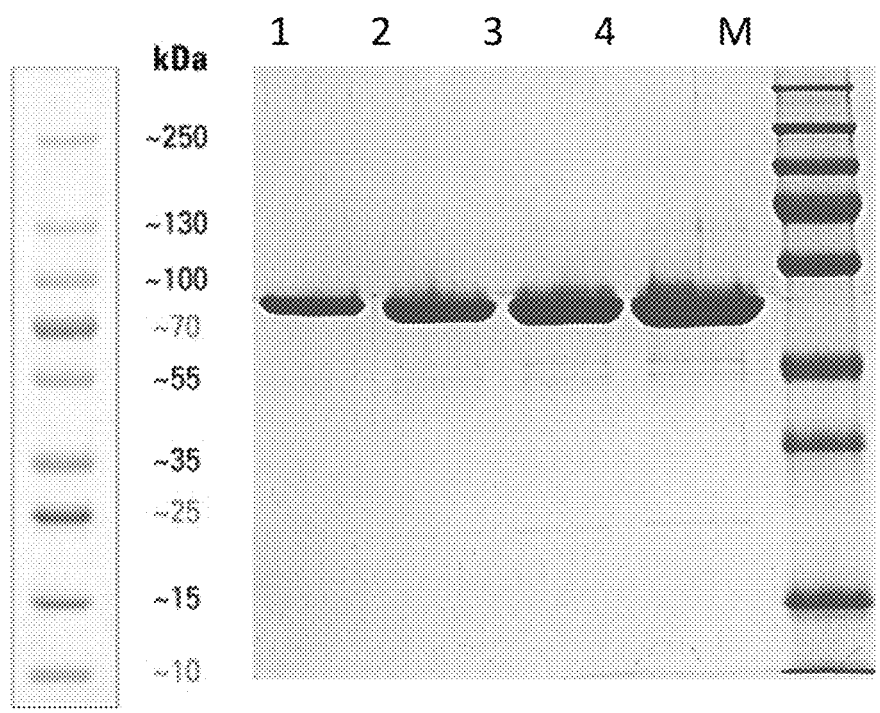
FIG. 6: Truncated PspA1 after diafiltration.

Capto Q fractions of 4, 5, 6, 7 and 8 were pooled, concentrated/diafiltered with 20 mM Potassium phosphate pH-6.8. The final recovery obtained was 100 mL of pspA1 with a concentration of 15.5 mg/mL of protein (Total PspA1 is 1550 mg) from Lot 1. Similar process was followed for Lot 2 and the final recovery obtained was 70 mL of pspA1 with a concentration of 16 mg/mL (Total PspA1 is 1120 mg) from Lot 2. The purified PspA1 from both Lot 1 and Lot 2 is 2670 mg from 16.2 L batch (Purified PspA1 yield of 164 mg/L). (FIG. 6)

Example 3: Construction of pBE114K

The expression vector pRSET A (commercial vector from Invitrogen) was modified by removing ampicillin resistance gene using DraI restriction digestion and ligating to SmaI digested kanamycin coding gene (obtained from pUC4 KIXX). This modified vector was designated as pRSET-km. Truncated PspA1 was expressed in *Escherichia coli* under PT7 promoter (SEQ ID NO: 11) of pRSET-km. A short stretch of DNA containing native terminators was included in the reverse primer used for further amplification of pspA1. Subsequently, the entire truncated pspA1gene along with its native terminator was amplified, digested with the restriction enzyme appended in the forward and reverse primers and cloned in pRSET-km vector. The resulted clone was designated as pBE114k (FIG. 10A). The expression vector along-with truncated PspA1 hereinafter is referred to as expression construct. The expression construct pBE114k was confirmed by restriction digestion (FIG. 10B). The sequence of truncated PspA1 gene along with its expression cassette was confirmed by DNA sequencing.

Expression of Truncated PspA1 pBE114k was transformed into *Escherichia coli* DH5a-T1R chemical competent cells (Procured from Invitrogen) and selected on LB plates with kanamycin as selectable marker. 40 recombinant *Escherichia coli* colonies were picked and analysed by PCR. All the 40 colonies were chosen for inducible expression of truncated PspA1. The recombinant colonies along with *Escherichia coli* (as negative control) were inoculated into 10 ml Terrific Broth with 25 µg/ml final concentration of kanamycin and incubated at 37° C. with shaking at 200 rpm. At mid log phase, 1 mM IPTG was added to induce the expression of PspA1 in *Escherichia coli* (pBE114k). The cultures were incubated at 30° C. with shaking at 200 rpm for 16h, after induction. After 16 h, the culture supernatants were checked for the expression of truncated PspA1. The cells were collected by centrifugation, lysed and loaded onto 12% SDS-PAGE and analysed for truncated PspA1 expression. A prominent band was seen around 65 kDa. Western analysis using N-terminal epitope specific PspA polyclonal antibody (SantaCruz) confirmed the expression of truncated PspA1. The expression analysis of recombinant clone 29 was confirmed for the expression of truncated PspA1 at least 3 times. Truncated PspA1 was initially purified from shake flask experiments using CHT type 1 and Capto Q impress.

Purification and Validation of Truncated PspA1

40 grams (wet weight) of cell pellet from *Escherichia coli* (pBE114k) was taken and re-suspended in 400 ml of 20 mM Potassium Phosphate buffer pH-6.8 containing 1 mg/ml Lysozyme and 1 mM PMSF. The cell suspension was lysed using high pressure homogenizer for 3 passes at 1000 psi. 400 mL of cell lysate with a total protein concentration of 4 mg/mL was diluted to 750 mL with 20 mM Potassium Phosphate buffer pH-6.8 and purified using CHT I resin followed by Capto Q Impress as a second chromatography.

Figure 11:
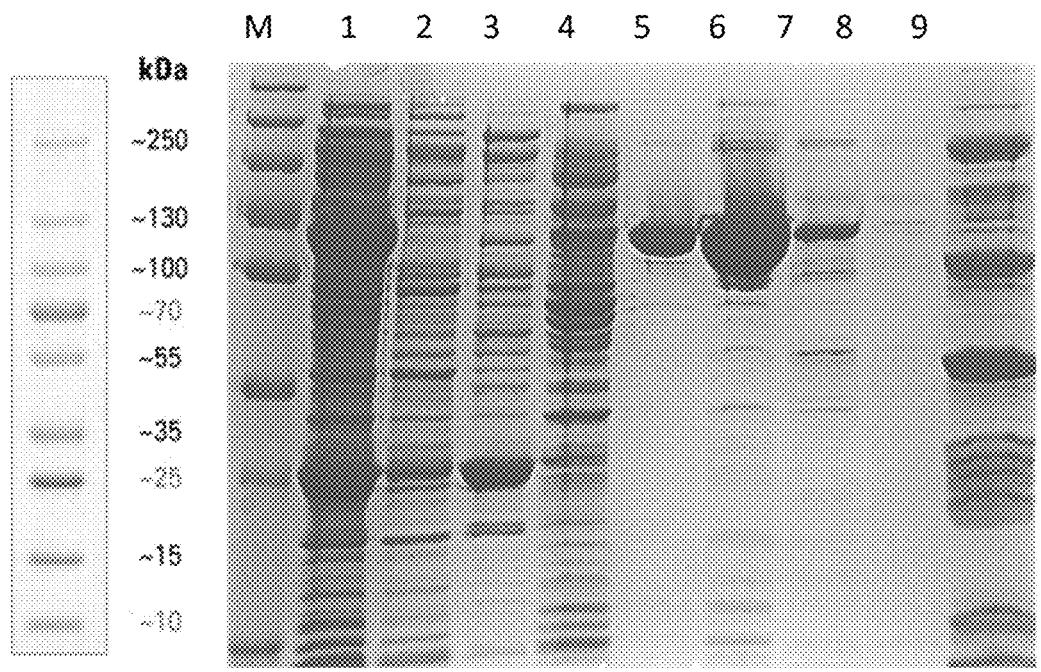
FIG. 11: Truncated PspA1 eluted from CHT I chromatography.

250 mL of CHT I resin was packed in HiScale 50/20 column. Resin was washed with sterile distilled water followed by equilibration with 5 column volumes (CV) of Buffer A. 750 mL diluted cell lysate was loaded onto the column and flow through was collected. Column was washed with 5 column volumes of Buffer A. PspA1 was eluted with Step gradient using 250 mM Potassium Phosphate pH-6.8, cond-29.5 ms/cm (Buffer B). The step gradient involved 5 CVs of Step-50% of Buffer B, 5 CVs of Step-80% of Buffer B and Column was stripped with 3 CVs of 0.5M Potassium Phosphate buffer pH-6.8, Cond-48 ms/cm (Buffer C). The flow rate was maintained at 40 mL/min for the entire run. The PspA1 protein peak fractions were collected manually, Elution fractions pool of 5, 6 and 7 of Step-80% B with a final volume of 350 mL (FIG. 11).

Figure 12:
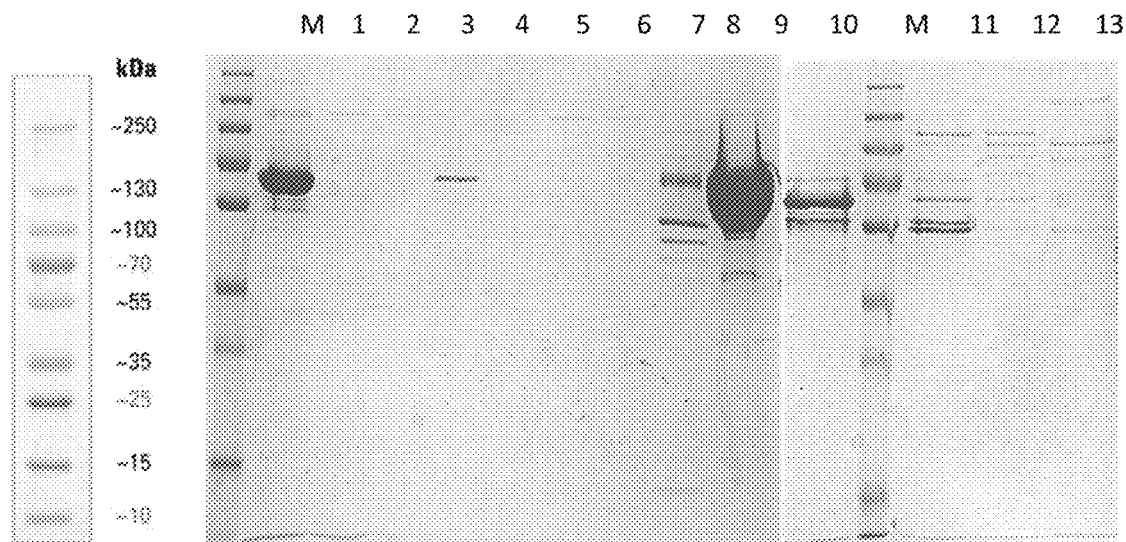
FIG. 12: Truncated PspA1 eluted from Capto Q Impress chromatography.

Capto Q Impress was used as a second chromatography step in PspA1 purification. 60 ml of Capto Q Impress resin was packed in XK 26/20 column. Resin was washed with sterile distilled water followed by equilibration with 5 column volumes (CV) of 20 mM Potassium Phosphate and 100 mM NaCl, pH-6.8, con-13.6 ms/cm (Buffer A). 350 mL of CHT I fraction was diluted to 700 mL with 1 mM Potassium Phosphate, pH-6.8, loaded onto the column and flow through was collected. Column was washed with 5 column volumes of Buffer A. PspA1 was eluted using linear gradient 10 CVs of Buffer B (20 mM Potassium Phosphate with 1 M NaCl, pH-6.2, cond-89 ms/cm) in a linear gradient of 0 to 40% B fractions were collected manually, fraction 4 to 8, 10 and 11 were 60 mL and 9 and 12 were 100 mL fractions (FIG. 12). Final step of 3 CVs of 100% B, 180 mL collected as fraction 13. The flow rate was maintained at 10 mL/min. The PspA1 protein was collected fraction 9 in linear gradient of 40% B was 100 mL.

Capto Q fraction of 9 was collected, concentrated/diafiltered with 20 mM Potassium phosphate pH-6.8. The final recovery obtained was 100 mL of PspA1 with a concentration of 5 mg/mL of protein (Total PspA1 protein is 500 mg) from 400 mL cell lysate with a concentration of 4 mg/mL. Recovery % is 31.25.

MALDI MS/MS analysis of the gel plug containing purified truncated PspA1 from SDS-PAGE gave a clear hit score of 223 with Pneumococcal surface protein A. 39% (FIG. 13) sequence coverage was shown with the PspA protein with NCBI protein id WP_050210652.1.

Figure 14:
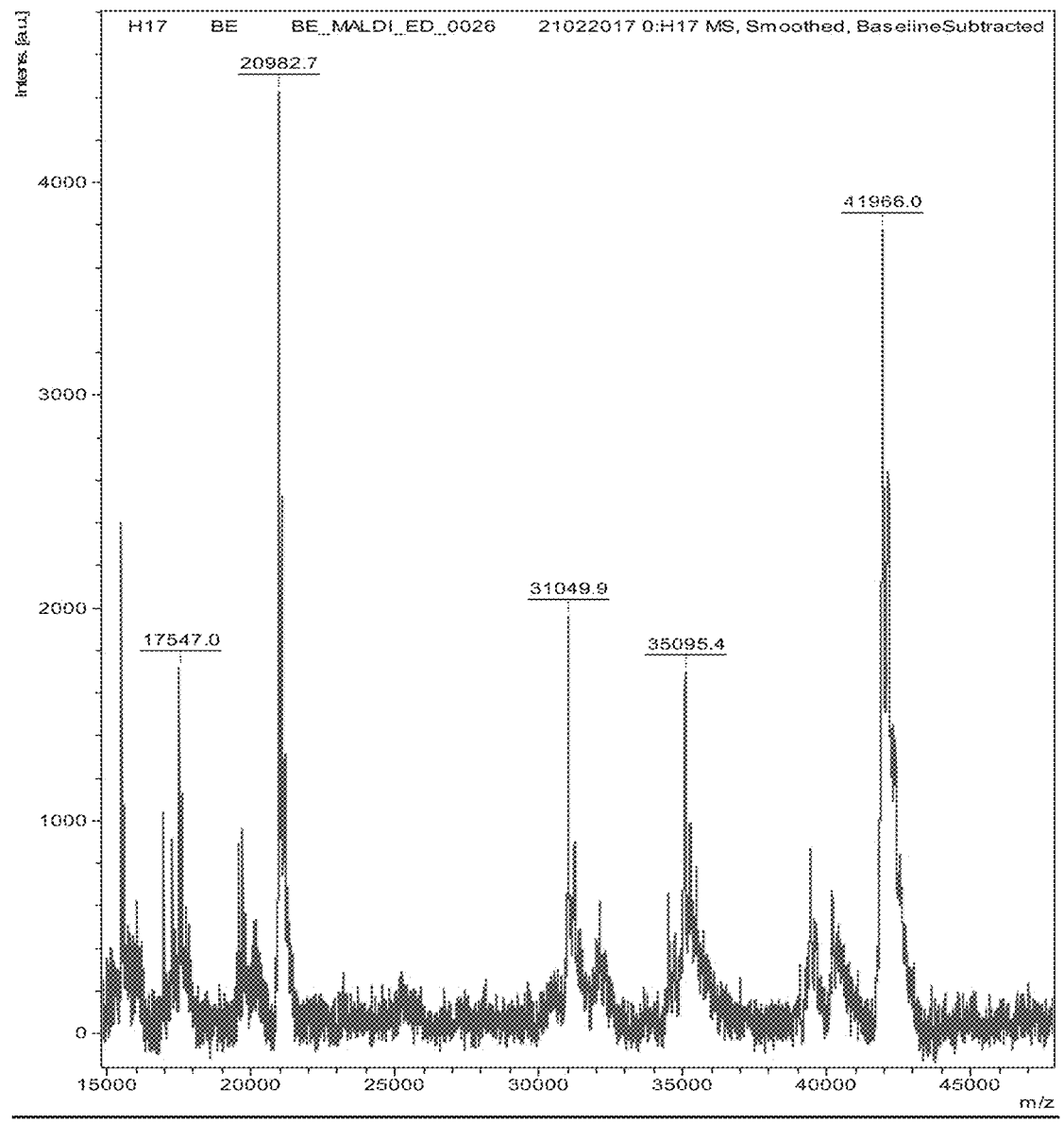
FIG. 14: Intact mass analysis of the truncated PspA1 expressed in *Escherichia coli*.

The intact molecular weight analysis showed the molecular weight of the truncated PspA1 expressed is 41.96 kDa. Intact mass analysis of the truncated PspA1 expressed in *Escherichia coli* showed 41966 Da (41.9 kDa), matches with the theoretical molecular weight of truncated PspA1. The peak at 20982.7 Da is a peak of molecule having a charge of 2 hence in the m/z the peak appears at half the intact mass of the truncated pspA1. (FIG. 14).

Example 4: Conjugation of Individual Pneumococcal Polysaccharide to Carrier Protein to Form Polysaccharide—Truncated PspA1 Conjugates Activation of Serotype 3 and Conjugation with Truncated pspA1

Approximately, 1:1 ratio of sized serotype 3 (6.0 mL of PS, concentration of 10 mg/mL) and CDAP (100 mg/mL in Acetonitrile (w/v)) was mixed in a glass vial and stirred for 1 min. pH of pneumococcal polysaccharide serotype 3 were adjusted to 9.25 with 0.2M Triethylamine and stirred for 3 min at room temperature (RT). Truncated PspA1 (4.0 mL of conc. 15.0 mg/mL) were added to the activated serotype 3 in the ratio of 1:1 (Truncated PspA1: Serotype 3).

pH of the reaction was adjusted to ~9.05 with 0.2M Triethylamine and the reaction was continued under stirring for 5 hours at room temperature and finally the reaction was quenched by adding excess concentration of glycine.

The reaction mixture was diafiltered using 100 kDa MWCO membrane and purified by size-exclusion chromatography wherein solid line is for polysaccharides and dashed lines for truncated pspA1 and five-hour reaction is represented by dotted line in chromatogram A (FIG. 7). The fractions were analysed by SEC-MALLS anthrone method and fractions containing conjugates were pooled and sterile filtered with 0.2μ filters. From now this material is called monovalent conjugate bulk (Serotype 3-Truncated PspA1 conjugate).

Activation of Serotype 6A and Conjugation with Truncated PspA1

Approximately, 1:1 ratio of sized serotype 6A (6.0 mL of PS, concentration of 10 mg/mL) and CDAP (100 mg/mL in Acetonitrile (w/v)) was mixed in a glass vial and stirred for 1 min. pH of pneumococcal polysaccharide serotype 6A were adjusted to 9.25 with 0.2M Triethylamine and stirred for 3 min at room temperature (RT). Truncated PspA1 (4.0 mL of conc. 15.0 mg/mL) were added to the activated serotype 6A in the ratio of 1:1 (Truncated PspA1: Serotype 6A).

pH of the reaction was adjusted to ~9.05 with 0.2M Triethylamine and the reaction was continued under stirring for 5 hours at room temperature and finally the reaction was quenched by adding excess concentration of glycine.

The reaction mixture was diafiltered using 100 kDa MWCO membrane and purified by size-exclusion chromatography wherein solid line is for polysaccharides and dashed lines for truncated pspA1 and five-hour reaction is represented by dotted line in chromatogram B (FIG. 7). The fractions were analysed by SEC-MALLS, anthrone method and fractions containing conjugates were pooled and sterile filtered with 0.2μ filters. From now this material is called monovalent conjugate bulk (Serotype 6A-Truncated PspA1 conjugate).

Activation of Serotype 6B and Conjugation with Truncated PspA1

Approximately, 1:1 ratio of sized serotype 6B (6.0 mL of PS, concentration of 10 mg/mL) and CDAP (100 mg/mL in Acetonitrile (w/v)) was mixed in a glass vial and stirred for 1 min. pH of pneumococcal polysaccharide serotype 6B were adjusted to 9.25 with 0.2M Triethylamine and stirred for 3 min at room temperature (RT). Truncated PspA1 (4.0 mL of conc. 15.0 mg/mL) were added to the activated serotype 6B in the ratio of 1:1 (Truncated PspA1: Serotype 6B).

pH of the reaction was adjusted to ~9.05 with 0.2M Triethylamine and the reaction was continued under stirring for 5 hours at room temperature and finally the reaction was quenched by adding excess concentration of glycine.

The reaction mixture was diafiltered using 100 kDa MWCO membrane and purified by size-exclusion chromatography wherein solid line is for polysaccharides and dashed lines for truncated PspA1 and five-hour reaction is represented by dotted line in chromatogram C (FIG. 7). The fractions were analysed by SEC-MALLS, anthrone method and fractions containing conjugates were pooled and sterile filtered with 0.2µ filters. From now this material is called monovalent conjugate bulk (Serotype 6B-Truncated PspA1 conjugate).

Example 5: Immunogenicity Study of the Conjugate Vaccine

Two formulations containing either 2.2 µg or 4.4 µg of Serotypes 3, 6A and 6B each conjugated to truncated PspA1 was prepared containing 2.2 µg of serotypes 1, 4, 5, 7F, 9V, 14, 18C, 19A, 19F, 22F, 23F and 33F each conjugated to CRM197. These conjugates were adsorbed onto A1-hydrogel.

Rabbits having a body weight of 1.5 to 2 kg were grouped in 7 animals each and were immunized with the above-mentioned conjugate formulations. Sera samples were analysed before and after immunization. Serum obtained from the immunized rabbits were analysed for the presence of polysaccharide specific antibody in an indirect ELISA.

Figure 8:
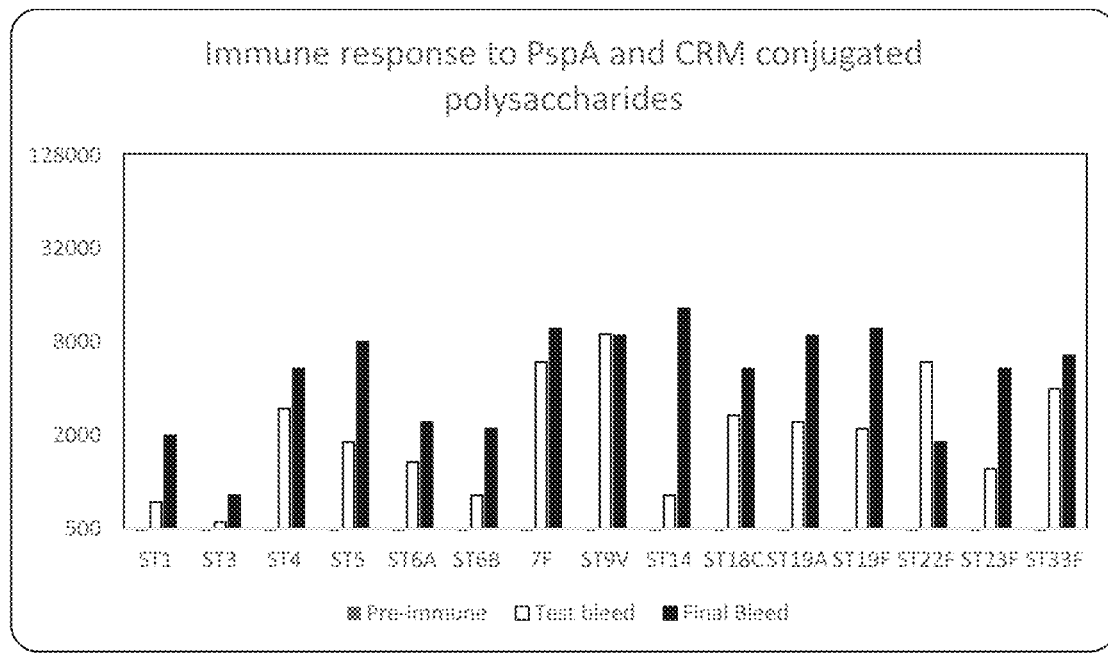
FIG. 8: Serum antibody titer of immunized rabbits against different conjugates of *Streptococcus pneumoniae* polysaccharide from serotypes 3, 6A, 6B (2.2 mcg) with truncated pspA1 carrier protein.
Figure 9:
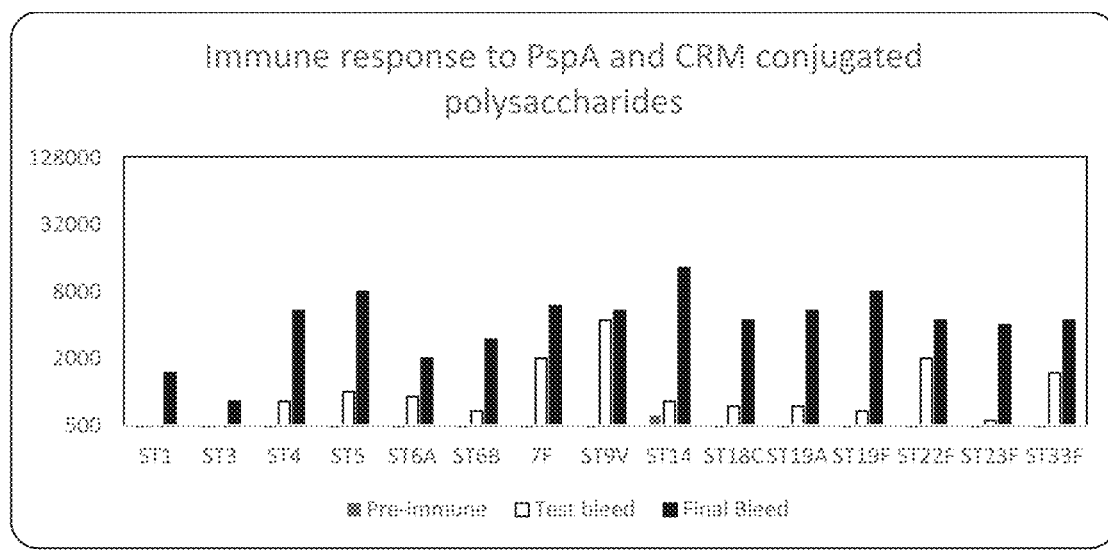
FIG. 9: Serum antibody titer of immunized rabbits against different conjugates of *Streptococcus pneumoniae* polysaccharide from serotypes 3, 6A, 6B (4.4 mcg) with truncated pspA1 carrier protein.

The serum antibody titer in the immunized rabbits were evaluated by indirect ELISA. Micro-titer plates coated with specific polysaccharides were reacted with the serum antibody. Rabbit serum prior to immunization, post $1^{st}$ and $2^{nd}$ dose was used for analysis wherein Y axis indicates antibody titer, which is arrived at using inverse of maximum dilution that gave ELISA $OD_{450}$ above the cut-off. Serum antibody titer in pre-immune rabbits were below detection limit. Open bar indicates titer after first dose of vaccine administration while the black solid bar indicates antibody titer after second dose of the vaccine (FIGS. 8 & 9). There was a dose dependent increase in both truncated pspA1 conjugated serotype as well as CRM197 conjugated serotype titers. The titers of CRM197 conjugated polysaccharide was not inhibited by the presence of truncated PspA1 conjugates and vice-versa. This indicates that the truncated PspA1 could be used as an alternative carrier protein for polysaccharide protein conjugate vaccine.

We claim:

1. A nucleic acid encoding a truncated pneumococcal surface protein A1 (PspA1) consisting of the nucleotide sequence of SEQ ID NO: 5.

2. An expression construct comprising the nucleic acid of claim 1.

3. An expression construct for high level expression of a truncated pneumococcal surface protein A1 (PspA1) having an amino acid sequence as set forth in SEQ ID NO: 3, comprising:
   a. a gene encoding the truncated PspA1 having a nucleotide sequence as set forth in SEQ ID NO: 5;
   b. an origin of replication;
   c. an antibiotic resistance gene;
   d. a promoter; and
   e. a ribosomal binding site.

4. The expression construct of claim 3, wherein the antibiotic resistance gene is a kanamycin resistance gene.

5. The expression construct of claim 3, wherein:
   a. the origin of replication is an ori R origin of replication;
   b. the antibiotic resistance gene is a kanamycin resistance gene; and
   c. the promoter is a $P_{tac}$ promoter.

6. The expression construct of claim 5, wherein
   a. the ori R origin of replication has a nucleotide sequence as set forth in SEQ ID NO: 12;
   b. the kanamycin resistance gene has a nucleotide sequence as set forth in SEQ ID NO: 1; and
   c. the $P_{tac}$ promoter has a nucleotide sequence as set forth in SEQ ID NO: 2, and wherein the expression construct further comprises a triose phosphate isomerase ribosomal binding site.

7. A recombinant host cell comprising the expression construct of claim 2.

8. The recombinant host cell of claim 7, wherein the host is *Corynebacterium glutamicum* or *Escherichia coli*.

9. A method for high level expression of *Streptococcus pneumoniae* truncated Pneumococcal Surface Protein A1 (PspA1), comprising culturing bacteria transformed with the expression construct of claim 2 and purifying the truncated PspA1 expressed by the expression construct.

10. The method of claim 9, wherein a yield of truncated PspA1 is about 500 mg/L, about 400 mg/L, about 300 mg/L, about 250 mg/L, about 220 mg/L, about 200 mg/L, about 180 mg/L, about 160 mg/L, about 150 mg/L, about 120 mg/L, or about 100 mg/L.

11. A recombinant host cell comprising the expression construct of claim 3.

12. The recombinant host cell of claim 11, wherein the host is *Corynebacterium glutamicum* or *Escherichia coli*.

13. A method for high level expression of *Streptococcus pneumoniae* truncated Pneumococcal Surface Protein A1 (PspA1), comprising culturing bacteria transformed with the expression construct of claim 3 and purifying the truncated PspA1 expressed by the expression construct.

14. The method of claim 13, wherein a yield of truncated PspA1 is about 500 mg/L, about 400 mg/L, about 300 mg/L, about 250 mg/L, about 220 mg/L, about 200 mg/L, about 180 mg/L, about 160 mg/L, about 150 mg/L, about 120 mg/L, or about 100 mg/L.

* * * * *

SEQUENCE LISTING

```
<160> NUMBER OF SEQ ID NOS: 29

<210> SEQ ID NO 1
<211> LENGTH: 795
<212> TYPE: DNA
<213> ORGANISM: Artificial Sequence
<220> FEATURE:
<223> OTHER INFORMATION: Synthetic:  Kanamycin Resistance Gene

<400> SEQUENCE: 1
atgattgaac aagatggatt gcacgcaggt tctccggccg cttgggtgga gaggctattc      60
ggctatgact gggcacaaca gacaatcggc tgctctgatg ccgccgtgtt ccggctgtca     120 gcgcagggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggagcc gggtcttgtc gatcagatga tctggacgaa     480
gagcatcagg ggctcgcgcc agccgaactg ttcgccaggc tcaaggcgcg catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctga                                                     795

<210> SEQ ID NO 2
<211> LENGTH: 30
<212> TYPE: DNA
<213> ORGANISM: Artificial Sequence
<220> FEATURE:
```

<223> OTHER INFORMATION: Synthetic: Hybrid Promoter

<400> SEQUENCE: 2
ttgacaatta atcatcggct cgtataatgt    30

<210> SEQ ID NO 3
<211> LENGTH: 310
<212> TYPE: PRT
<213> ORGANISM: Streptococcus pneumoniae

<400> SEQUENCE: 3

```
Glu Asp Ala Pro Val Ala Asn Gln Ser Lys Ala Glu Lys Asp Tyr Asp
1               5                   10                  15

Ala Ala Lys Arg Asp Ala Glu Asn Ala Lys Lys Ala Leu Glu Asp Ala
            20                  25                  30

Lys Arg Ala Gln Lys Lys Tyr Lys Asp Asp Gln Lys Ile Thr Glu Glu
        35                  40                  45

Lys Ala Glu Glu Glu Lys Ala Ser Gln Gln Gln Lys Ala Asn
    50                  55                  60

Leu Asp Tyr Gln Gln Lys Leu Arg Lys Tyr Ile Asn Glu Lys Asp Ser
65                  70                  75                  80

Lys Lys Arg Ser Met Leu Gln Lys Glu Met Glu Ala Glu Arg Lys
                85                  90                  95

Asp Lys Glu Lys Gln Ala Glu Phe Lys Lys Ile Arg Glu Lys Val Ile
                100                 105                 110

Pro Ser Ala Glu Glu Leu Thr Glu Thr Arg Arg Lys Ala Glu Glu Ala
            115                 120                 125

Glu Ala Lys Glu Pro Glu Leu Thr Lys Lys Val Lys Glu Ala Glu Glu
    130                 135                 140

Lys Val Thr Glu Ala Lys Gln Lys Leu Asp Ala Glu Arg Ala Lys Glu
145                 150                 155                 160

Val Ala Leu Gln Ala Lys Ile Ala Glu Leu Glu Asn Glu Val His Arg
                165                 170                 175

Leu Glu Thr Lys Leu Lys Glu Ile Asp Glu Ser Asp Ser Glu Asp Tyr
            180                 185                 190

Val Lys Glu Gly Leu Arg Ala Pro Leu Gln Ser Glu Leu Asp Ala Lys
        195                 200                 205

Gln Ala Lys Leu Ser Lys Leu Glu Glu Leu Ser Asp Lys Ile Asp Glu
    210                 215                 220

Leu Asp Ala Glu Ile Ala Lys Leu Glu Lys Asp Val Glu Asp Phe Lys
225                 230                 235                 240

Asn Ser Asp Gly Glu Tyr Ser Ala Leu Tyr Leu Glu Ala Ala Glu Lys
                245                 250                 255

Asp Leu Ala Ala Lys Lys Ala Glu Leu Glu Lys Thr Glu Ala Asp Leu
            260                 265                 270

Lys Lys Ala Val Asp Glu Pro Glu Lys Pro Ala Pro Ala Pro Glu Thr
        275                 280                 285

Pro Ala Pro Glu Ala Pro Ala Glu Gln Pro Lys Pro Ala Pro Ala Pro
    290                 295                 300

Gln Pro Ala Pro Ala Pro
305                 310
```

<210> SEQ ID NO 4
<211> LENGTH: 369
<212> TYPE: PRT
<213> ORGANISM: Streptococcus pneumoniae

<400> SEQUENCE: 4

```
Glu Asp Ala Pro Val Ala Asn Gln Ser Lys Ala Glu Lys Asp Tyr Asp
1               5                   10                  15
Ala Ala Lys Arg Asp Ala Glu Asn Ala Lys Lys Ala Leu Glu Asp Ala
                20                  25                  30
Lys Arg Ala Gln Lys Lys Tyr Lys Asp Asp Gln Lys Ile Thr Glu Glu
            35                  40                  45
Lys Ala Glu Glu Glu Lys Lys Ala Ser Gln Glu Gln Gln Lys Ala Asn
50                  55                  60
Leu Asp Tyr Gln Gln Lys Leu Arg Lys Tyr Ile Asn Glu Lys Asp Ser
65                  70                  75                  80
Lys Lys Arg Ser Met Leu Gln Lys Glu Met Glu Glu Ala Glu Arg Lys
                85                  90                  95
Asp Lys Glu Lys Gln Ala Glu Phe Lys Lys Ile Arg Glu Lys Val Ile
                100                 105                 110
Pro Ser Ala Glu Glu Leu Thr Glu Thr Arg Arg Lys Ala Glu Glu Ala
            115                 120                 125
Glu Ala Lys Glu Pro Glu Leu Thr Lys Lys Val Lys Glu Ala Glu Glu
130                 135                 140
Lys Val Thr Glu Ala Lys Gln Lys Leu Asp Ala Glu Arg Ala Lys Glu
145                 150                 155                 160
Val Ala Leu Gln Ala Lys Ile Ala Glu Leu Glu Asn Glu Val His Arg
                165                 170                 175
Leu Glu Thr Lys Leu Lys Glu Ile Asp Glu Ser Asp Ser Glu Asp Tyr
                180                 185                 190
Val Lys Glu Gly Leu Arg Ala Pro Leu Gln Ser Glu Leu Asp Ala Lys
            195                 200                 205
Gln Ala Lys Leu Ser Lys Leu Glu Glu Leu Ser Asp Lys Ile Asp Glu
210                 215                 220
Leu Asp Ala Glu Ile Ala Lys Leu Glu Lys Asp Val Glu Asp Phe Lys
225                 230                 235                 240
Asn Ser Asp Gly Glu Tyr Ser Ala Leu Tyr Leu Glu Ala Ala Glu Lys
                245                 250                 255
Asp Leu Ala Ala Lys Lys Ala Glu Leu Glu Lys Thr Glu Ala Asp Leu
                260                 265                 270
Lys Lys Ala Val Asp Glu Pro Glu Lys Pro Ala Pro Ala Pro Glu Thr
            275                 280                 285
Pro Ala Pro Glu Ala Pro Ala Glu Gln Pro Lys Pro Ala Pro Ala Pro
290                 295                 300
Gln Pro Ala Pro Ala Pro Lys Pro Glu Lys Pro Ala Glu Gln Pro Lys
305                 310                 315                 320
Pro Glu Lys Thr Asp Asp Gln Ala Glu Glu Asp Tyr Ala Arg Arg
                325                 330                 335
Ser Glu Glu Glu Tyr Asn Arg Leu Thr Gln Gln Pro Pro Lys Ala
                340                 345                 350
Glu Lys Pro Ala Pro Ala Pro Lys Pro Glu Gln Pro Ala Pro Ala Pro
            355                 360                 365
Lys
```

<210> SEQ ID NO 5
<211> LENGTH: 933
<212> TYPE: DNA
<213> ORGANISM: Streptococcus pneumoniae

<400> SEQUENCE: 5

```
gaagacgctc ctgtagctaa ccagtctaaa gctgagaaag actatgatgc agcgaagaga        60
gatgctgaga atgcgaaaaa agctttagag gacgcaaaac gtgcgcagaa aaatataag        120
gatgatcaga agataactga ggagaaagcg gaagaagaaa aaaagcttc tcaagagcaa        180
caaaaagcaa atctggacta tcaacaaaag ttgaggaaat atattaacga aaaagactcc        240
aaaaaaagat ctatgcttca gaaagaaatg gaggaagctg agagaaaaga taaggaaaaa        300
caagcagaat ttaagaagat tagagaaaag gtgattccta gcgcggaaga gttaacagag        360
actagacgaa aagcagaaga ggctgaagca aagaaccag agcttactaa aaagtaaaa        420
gaagctgagg aaaaagttac tgaagccaaa caaaaattgg atgctgaacg tgctaaagaa        480
gttgctcttc aagccaaaat cgctgagttg aaaatgaag ttcatagact agaaacaaaa        540
ctcaaagaga ttgatgaatc tgactcagaa gattatgtta agaaggtct ccgtgctcct        600
cttcaatctg aattggatgc taagcaagct aaactatcaa acttgaaga gttgagtgat        660
aagattgatg agttagacgc tgaaattgca aaacttgaaa aagatgtaga agatttcaaa        720
aactcagacg gtgaatattc tgcattatat cttgaagctg cagaaaaaga tttagctgct        780
aaaaaagctg aattagaaaa aactgaagct gacctcaaga aagcagttga tgagccagaa        840
aaaccagctc cagctccaga aactccagcc ccagaagcac cagctgaaca accaaaacca        900
gcgccggctc ctcaaccagc tcctgcacca taa                                     933
```

<210> SEQ ID NO 6
<211> LENGTH: 1110
<212> TYPE: DNA
<213> ORGANISM: Streptococcus pneumoniae

<400> SEQUENCE: 6

```
gaagacgctc ctgtagctaa ccagtctaaa gctgagaaag actatgatgc agcgaagaga        60
gatgctgaga atgcgaaaaa agctttagag gacgcaaaac gtgcgcagaa aaatataag        120
gatgatcaga agataactga ggagaaagcg gaagaagaaa aaaagcttc tcaagagcaa        180
caaaaagcaa atctggacta tcaacaaaag ttgaggaaat atattaacga aaaagactcc        240
aaaaaaagat ctatgcttca gaaagaaatg gaggaagctg agagaaaaga taaggaaaaa        300
caagcagaat ttaagaagat tagagaaaag gtgattccta gcgcggaaga gttaacagag        360
actagacgaa aagcagaaga ggctgaagca aagaaccag agcttactaa aaagtaaaa        420
gaagctgagg aaaaagttac tgaagccaaa caaaaattgg atgctgaacg tgctaaagaa        480
gttgctcttc aagccaaaat cgctgagttg aaaatgaag ttcatagact agaaacaaaa        540
ctcaaagaga ttgatgaatc tgactcagaa gattatgtta agaaggtct ccgtgctcct        600
cttcaatctg aattggatgc taagcaagct aaactatcaa acttgaaga gttgagtgat        660
aagattgatg agttagacgc tgaaattgca aaacttgaaa aagatgtaga agatttcaaa        720
aactcagacg gtgaatattc tgcattatat cttgaagctg cagaaaaaga tttagctgct        780
aaaaaagctg aattagaaaa aactgaagct gacctcaaga aagcagttga tgagccagaa        840
aaaccagctc cagctccaga aactccagcc ccagaagcac cagctgaaca accaaaacca        900
gcgccggctc ctcaaccagc tcccgcacca aaaccagaga agccagctga acaaccaaaa        960
ccagaaaaaa cagatgatca acaagctgaa gaagactatg ctcgtagatc agaagaagaa       1020
tataaccgct tgactcaaca gcaaccgcca aaagcagaaa aaccagctcc cgcaccaaaa       1080
```

```
ccagagcaac cagctcctgc accaaaataa                                    1110

<210> SEQ ID NO 7
<211> LENGTH: 20
<212> TYPE: DNA
<213> ORGANISM: Corynebacterium glutamicum

<400> SEQUENCE: 7
tagaaaggtg tgtttcaccc                                                 20

<210> SEQ ID NO 8
<211> LENGTH: 93
<212> TYPE: DNA
<213> ORGANISM: Streptococcus pneumoniae

<400> SEQUENCE: 8
atgaataaga aaaaaatgat tttaacaagt ctagccagcg tcgctatctt aggggctggt    60
tttgttgcgt cttcgcctac tgttgtaaga gca                                  93

<210> SEQ ID NO 9
<211> LENGTH: 31
<212> TYPE: PRT
<213> ORGANISM: Streptococcus pneumoniae

<400> SEQUENCE: 9

Met Asn Lys Lys Lys Met Ile Leu Thr Ser Leu Ala Ser Val Ala Ile
1               5                   10                  15

Leu Gly Ala Gly Phe Val Ala Ser Ser Pro Thr Val Val Arg Ala
            20                  25                  30

<210> SEQ ID NO 10
<211> LENGTH: 38
<212> TYPE: DNA
<213> ORGANISM: Streptococcus pneumoniae

<400> SEQUENCE: 10
aaattaaagc atgttaagaa catttgacat tttaatttt                            38

<210> SEQ ID NO 11
<211> LENGTH: 19
<212> TYPE: DNA
<213> ORGANISM: Artificial Sequence
<220> FEATURE:
<223> OTHER INFORMATION: Synthetic:   PT7 Promoter

<400> SEQUENCE: 11
taatacgact cactatagg                                                  19

<210> SEQ ID NO 12
<211> LENGTH: 1854
<212> TYPE: DNA
<213> ORGANISM: Corynebacterium diphtheriae

<400> SEQUENCE: 12
gaattcggtg aggttatggc ggagggttgc gaggtctagg agaacagagg aagtcatgct    60
ttgaagcata taagctgccc tgcccctcaa ggttttcttc aagtgaggtt ttatctaact   120
gcctaacggc aggggaaccg tatattgctt acgtatgag accccttaaa cgtccggata    180
gtcaccgctc ttctttagct ccgcgacatg cctagcaacc gtggcgcgag agactcctac   240 ctctgccccct atttcagccc acgtgggaac tgtccctgtc tggaaatact gatcgttcac   300
catttggcta atacgggact tcgtagatcg tccttgagcc ttttttcttac ggtgcgtctt   360
```

```
ttcaagcttc gacctttgtg cttgcgcata tttgccctcg gggtctgttt tccagcgttg    420
tgcggctttt tgtccgcctc tgcgtccat cgtggccaag ctttccgct cgctgctggt      480 ggctttacct ggtgcgttag agccgctgta ggtctcgctc ttggattggg cgacataccc    540
gcgcacgcgc cttgccatgg tttggcggtc gcgcatgggt ggcatctcgt tgtcgcggcc   600
tgcaccgccg tgggtgtgtg cgacgttgta ggcgtgctca taggcgtcga tgattgctgc   660
gtctgtcagg cgttggcctt gctggcgcaa gcggtgccca gtcttaagcg catgtctaaa   720
ggctgtttcg tcgcgtgctg cggttccttg acaatccag agcacacgca caccgtcgat    780
aagttccggg tcatactggt cgagaccacc ggcgatttcc cgtctacgt cctgggcgag    840 tgctttgaat gcttgggctt cttcacggcg ggtcttgacc gcgttgataa gttcgcggcc   900
agagctgaat gctgcgcgtg gggtgggtt gaactggtcg tgtcctgcca tatcccttac    960
ctgctttatc aagtctccaa ggcgcatcac ccggttgtgc tgcctatacc aacgataagc   1020
ggtaggggct ttgcctgtgt agaacgggtt gcggctaaag cggtgggaaa agtgcgggtc   1080
atggtctaaa agctcaccca gcacacgcgt ggttgctgca agaagcttca tctgcgcaga   1140
tttaccgtta cggtcagcgt agacagggtc aataagccat atgaactggg ctttgccgtt   1200
agttgggtta atacccaccc aggctggccc gacgctatga gtaatcagtg agcgcaccac   1260
gtcgcggacg tacgggttta agtctgcggg gtcaccgcct gcggtaccta cttggtcaac   1320
gtctacgacc aggacggcgg cgtactgctt ggtggtgagc atggcgtact cgcaccgtcc   1380
taaagcatca gtctcgaagc gatacatacg cggcgagttc gtgccgtcag cgttgcgtcg   1440
ataggccttt ttaaagtctc gtgtgactga accgtggagt acatcgcggc ctagatgatc   1500
gcgtaaaagg tcgcggtcac tggcagatgc tggggtgttg tccagtccac cacggtcgcg   1560
ctcgacgcgg gtaggtgttt tagtgtgcgc attctgcgca tgagtctgta aactcatgac   1620
cgtgatttct cccaggtgtg tgctgggtga taagcgaaag tcatcgggtt gccgcccggt   1680
ggctttcttc gtttttcatt gtctttccct gactctaaat gacaccggtg ttatttacta   1740
gccatgacac gcgaaaaata tgccttttac ctgcggttac gtatggctag acatatggca   1800
agctatacgt aaccgcgttt cagctgcaca gggctgtctg cgcagattta ccat         1854
```

<210> SEQ ID NO 13
<211> LENGTH: 627
<212> TYPE: DNA
<213> ORGANISM: Artificial Sequence
<220> FEATURE:
<223> OTHER INFORMATION: Synthetic: rrnB terminator

<400> SEQUENCE: 13

```
cggcactggc cgtcgtttta caacgtcgtg actgggaaaa ccctggcgtt acccaactta     60
atcgccttgc agcacatccc cctttcgcca gctggctaat agcgaagagg cccgcaccga   120
tcgcccttcc caacagttgc gcagcctgaa tggcgatggc tgttttggcg gatgagagaa   180
gattttcagc ctgatacaga ttaaatcaga acgcagaagc ggtctgataa acagaatttt   240
gcctggcggc agtagcgcgg tggtcccacc tgaccccatg ccgaactcag aagtgaaacg   300
ccgtagcgcc gatggtagtg tggggtctcc ccatgcgaga gtagggaact gccaggcatc   360
aaataaaacg aaaggctcag tcgaaagact gggcctttcg ttttatctgt tgtttgtcgg   420
tgaacgctct cctgagtagg acaaatccgc cgggagcgga tttgaacgtt gcgaagcaac   480
ggcccggagg gtggcgggca ggacgcccgc cataaactgc caggcatcaa attaagcaga   540
```

```
aggccatcct gacggatggc cttttttgcgt ttctacaaac tcttttgttt atttttctaa      600
atacattcaa atatgtatcc gctcatg                                           627

<210> SEQ ID NO 14
<211> LENGTH: 3784
<212> TYPE: DNA
<213> ORGANISM: Artificial Sequence
<220> FEATURE:
<223> OTHER INFORMATION: Synthetic: pBE31C

<400> SEQUENCE: 14
actagtctga aatgagctgt tgacaattaa tcatcggctc gtataatgtg tggaattgtg       60
agcggataac aatttcacac aggaaactag gcaccccagg ctttacactt tatgcttccg      120
gctcgtatgt tgtgtggaat tgtgagcgga taacaatttc acacaggaaa cagctatgac      180
catgattacg aattcccggg gatccgtcga cctgcagcca agcttggcac tggccgtcgt      240
tttacaacgt cgtgactggg aaaaccctgg cgttacccaa cttaatcgcc ttgcagcaca      300
tccccctttc gccagctggc taatagcgaa gaggcccgca ccgatcgccc ttcccaacag      360
ttgcgcagcc tgaatggcga tggctgtttt ggcggatgag agaagatttt cagcctgata      420
cagattaaat cagaacgcag aagcggtctg ataaaacaga atttgcctgg cggcagtagc      480
gcggtggtcc cacctgaccc catgccgaac tcagaagtga acgccgtag cgccgatggt      540 agtgtggggt ctccccatgc gagagtaggg aactgccagg catcaaataa acgaaaggc      600 tcagtcgaaa gactgggcct ttcgttttat ctgttgtttg tcggtgaacg ctctcctgag      660
taggacaaat ccgccgggag cggatttgaa cgttgcgaag caacggcccg gagggtggcg      720
ggcaggacgc ccgccataaa ctgccaggca tcaaattaag cagaaggcca tcctgacgga      780
tggccttttt gcgtttctac aaactctttt gtttattttt ctaaatacat tcaaatatgt      840
atccgctcat gtttaaaact agtccgaggt cccgggggtt gggcgtcgct tggtcggtca      900
tttcgaaccc cagagtcccg ctcagaagaa ctcgtcaaga aggcgataga aggcgatgcg      960
ctgcgaatcg ggagcggcga taccgtaaag cacgaggaag cggtcagccc attcgccgcc     1020
aagctcttca gcaatatcac gggtagccaa cgctatgtcc tgatagcggt ccgccacacc     1080
cagccggcca cagtcgatga atccagaaaa gcggccattt tccaccatga tattcggcaa     1140
gcaggcatcg ccatgggtca cgacgagatc ctcgccgtcg gcatgcgcg ccttgagcct     1200 ggcgaacagt tcggctggcg cgagcccctg atgctcttcg tccagatcat ctgatcgaca     1260
agacccggct ccatcccgag tacgtgctcg ctcgatgcga tgtttcgctt ggtggtcgaa     1320
tgggcaggta gccggatcaa gcgtatgcag ccgccgcatt gcatcagcca tgatggatac     1380
tttctcggca ggagcaaggt gagatgacag gagatcctgc cccggcactt cgcccaatag     1440
cagccagtcc cttcccgctt cagtgacaac gtcgagcaca gctgcgcaag gaacgcccgt     1500
cgtggccagc cacgatagcc gcgctgcctc gtcctgcagt tcattcaggg caccggacag     1560
gtcggtcttg acaaaaagaa ccgggcgccc ctgcgctgac agccggaaca cggcggcatc     1620
agagcagccg attgtctgtt gtgcccagtc atagccgaat agcctctcca cccaagcggc     1680
cggagaacct gcgtgcaatc catcttgttc aatcatgcga acgatcctc atcctgtctc     1740 ttgatcagat cttgatcccc tgcgccatca gatccttggc ggcaagaaag ccatccagtt     1800
tactttgcag ggcttcccaa ccttaccaga gggcgcccca gctggcaatt ccggttcgct     1860
tgctgtccat aaaaccgccc agtctagcta tcgccatccc gggaccttct agtagatctg     1920
aattcggtga ggttatggcg gagggttgcg aggtctagga gaacagagga agtcatgctt     1980
```

```
tgaagcatat aagctgccct gcccctcaag gttttcttca agtgaggttt tatctaactg    2040
cctaacggca ggggaaccgt atattgctta cggtatgaga ccccttaaac gtccggatag    2100
tcaccgctct tctttagctc cgcgacatgc ctagcaaccg tggcgcgaga gactcctacc    2160
tctgccccta tttcagccca cgtgggaact gtccctgtct ggaaatactg atcgttcacc    2220
atttggctaa tacgggactt cgtagatcgt ccttgagcct ttttcttacg gtgcgtcttt    2280
tcaagcttcg accttttgtgc ttgcgcatat ttgccctcgg ggtctgtttt ccagcgttgt    2340
gcggcttttt gtccgcctct gcgtcccatc gtggccaagg ctttccgctc gctgctggtg    2400
gctttacctg gtgcgttaga gccgctgtag gtctcgctct tggattgggc gacatacccg    2460
cgcacgcgcc ttgccatggt ttggcggtcg cgcatgggtg gcatctcgtt gtcgcggcct    2520
gcaccgccgt gggtgtgtgc gacgttgtag gcgtgctcat aggcgtcgat gattgctgcg    2580
tctgtcaggc gttggccttg ctggcgcaag cggtggccag tcttaagcgc atgtctaaag    2640
gctgtttcgt cgcgtgctgc ggttccttgg acaatccaga gcacacgcac accgtcgata    2700
agttccgggt catactggtc gagaccaccg gcgatttccg cgtctacgtc ctgggcgagt    2760
gctttgaatg cttgggcttc ttcacggcgg gtcttgaccg cgttgataag ttcgcggcca    2820
gagctgaatt gctggcgtgg ggtggggttg aactggtcgt gtcctgccat atcccttacc    2880
tgctttatca agtctccaag gcgcatcacc cggttgtgct gcctatacca acgataagcg    2940
gtaggggctt tgcctgtgta aacgggttg cggctaaagc ggtgggaaaa gtgcgggtca    3000
tggtctaaaa gctcacccag cacacgcgtg gttgctgcaa gaagcttcat ctgcgcagat    3060
ttaccgttac ggtcagcgta gacagggtca ataagccata tgaactgggc tttgccgtta    3120
gttgggttaa tacccaccca ggctggcccg acgctatgag taatcagtga gcgcaccacg    3180
tcgcggacgt acgggtttaa gtctgcgggg tcaccgcctg cggtacctac ttggtcaacg    3240
tctacgacca ggacggcggc gtactgcttg gtggtgagca tggcgtactc gcaccgtcct    3300
aaagcatcag tctcgaagcg atacatacgc ggcgagttcg tgccgtcagc gttgcgtcga    3360 taggccttt taaagtctcg tgtgactgaa ccgtggagta catcgcggcc tagatgatcg    3420
cgtaaaaggt cgcggtcact ggcagatgct ggggtgttgt ccagtccacc acggtcgcgc    3480
tcgacgcggg taggtgtttt agtgtgcgca ttctgcgcat gagtctgtaa actcatgacc    3540
gtgatttctc ccaggtgtgt gctgggtgat aagcgaaagt catcggggttg ccgcccggtg    3600 gctttcttcg ttttcattg tctttccctg actctaaatg acaccggtgt tatttactag    3660
ccatgacacg cgaaaatat gccttttacc tgcggttacg tatggctaga catatggcaa    3720
gctatacgta accgcgtttc agctgcacag ggctgtctgc gcagatttac catagatcta    3780
ctag                                                                3784
```

<210> SEQ ID NO 15
<211> LENGTH: 5501
<212> TYPE: DNA
<213> ORGANISM: Artificial Sequence
<220> FEATURE:
<223> OTHER INFORMATION: Synthetic: pBE117

<400> SEQUENCE: 15

```
actagtctga aatgagctgt tgacaattaa tcatcggctc gtataatgtg tggaattgtg      60
agcggataac aatttcacac aggaaactag gcacccagg ctttacactt tatgcttccg      120
gctcgtatgt tgtgtggaat tgtgagcgga taacaattc acacaggaaa cagctatgac      180
```

```
catgattacg aattcccggg gatcctagaa aggtgtgttt cacccatgaa taagaaaaaa      240
atgattttaa caagtctagc cagcgtcgct atcttagggg ctggttttgt tgcgtcttcg      300
cctactgttg taagagcaga agacgctcct gtagctaacc agtctaaagc tgagaaagac      360
tatgatgcag cgaagagaga tgctgagaat gcgaaaaaag ctttagagga cgcaaaacgt      420
gcgcagaaaa aatataagga tgatcagaag ataactgagg agaaagcgga agaagaaaaa      480
aaagcttctc aagagcaaca aaaagcaaat ctggactatc aacaaaagtt gaggaaatat      540
attaacgaaa aagactccaa aaaagatct atgcttcaga agaaatggga ggaagctgag       600
agaaaagata ggaaaaaaca agcagaattt aagaagatta gagaaaaggt gattcctagc      660
gcggaagagt taacagagac tagacgaaaa gcagaagagg ctgaagcaaa agaaccagag      720
cttactaaaa aagtaaaaga agctgaggaa aaagttactg aagccaaaca aaaattggat      780
gctgaacgtg ctaaagaagt tgctcttcaa gccaaaatcg ctgagttgga aaatgaagtt      840
catagactag aaacaaaact caaagagatt gatgaatctg actcagaaga ttatgttaaa      900
gaaggtctcc gtgctcctct tcaatctgaa ttggatgcta agcaagctaa actatcaaaa      960
cttgaagagt tgagtgataa gattgatgag ttagacgctg aaattgcaaa acttgaaaaa     1020
gatgtagaag atttcaaaaa ctcagacggt gaatattctg cattatatct tgaagctgca     1080
gaaaaagatt tagctgctaa aaaagctgaa ttagaaaaaa ctgaagctga cctcaagaaa     1140
gcagttgatg agccagaaaa accagctcca gctccagaaa ctccagcccc agaagcacca     1200
gctgaacaac caaaaccagc gccggctcct caaccagctc ctgcaccata aaaattaaag     1260
catgttaaga acatttgaca ttttaatttc ggcactggcc gtcgttttac aacgtcgtga     1320
ctgggaaaac cctggcgtta cccaacttaa tcgccttgca gcacatcccc ctttcgccag     1380
ctggctaata gcgaagaggc ccgcaccgat cgcccttccc aacagttgcg cagcctgaat     1440
ggcgatggct gttttggcgg atgagagaag attttcagcc tgatacagat taaatcagaa     1500
cgcagaagcg gtctgataaa acagaatttg cctggcggca gtagcgcggt ggtcccacct     1560
gaccccatgc cgaactcaga agtgaaacgc cgtagcgccg atggtagtgt ggggtctccc     1620
catgcgagag tagggaactg ccaggcatca aataaaacga aaggctcagt cgaaagactg     1680
ggcctttcgt tttatctgtt gtttgtcggt gaacgctctc ctgagtagga caaatccgcc     1740
gggagcggat ttgaacgttg cgaagcaacg gcccggaggg tggcgggcag gacgcccgcc     1800
ataaactgcc aggcatcaaa ttaagcagaa ggccatcctg acggatggcc ttttgcgt     1860 tctacaaact cttttgttta tttttctaaa tacattcaaa tatgtatccg ctcatgggat     1920
ccgtcgacct gcagccaagc ttggcactgg ccgtcgtttt acaacgtcgt gactgggaaa     1980
accctggcgt tacccaactt aatcgccttg cagcacatcc ccctttcgcc agctggctaa     2040
tagcgaagag gcccgcaccg atcgcccttc ccaacagttg cgcagcctga atggcgatgg     2100
ctgttttggc ggatgagaga agattttcag cctgatacag attaaatcag aacgcagaag     2160
cggtctgata aaacagaatt tgcctggcgg cagtagcgcg gtggtccac ctgacccat       2220 gccgaactca gaagtgaaac gccgtagcgc cgatggtagt gtgggtctc cccatgcgag      2280 agtagggaac tgccaggcat caaataaaac gaaaggctca gtcgaaagac tgggcctttc     2340
gttttatctg ttgtttgtcg gtgaacgctc tcctgagtag gacaaatccg ccgggagcgg     2400
atttgaacgt tgcgaagcaa cggcccggag ggtggcgggc aggacgcccg ccataaactg     2460
ccaggcatca aattaagcag aaggccatcc tgacggatgg ccttttgcg tttctacaaa      2520 ctcttttgtt tattttttcta aatacattca aatatgtatc cgctcatgtt taaaactagt    2580
```

```
ccgaggtccc gggggttggg cgtcgcttgg tcggtcattt cgaacCccag agtcccgctc   2640
agaagaactc gtcaagaagg cgatagaagg cgatgcgctg cgaatcggga gcggcgatac   2700
cgtaaagcac gaggaagcgg tcagcccatt cgccgccaag ctcttcagca atatcacggg   2760
tagccaacgc tatgtcctga tagccggtccg ccacacccag ccggccacag tcgatgaatc   2820
cagaaaagcg gccatttTcc accatgatat tcggcaagca ggcatcgcca tgggtcacga   2880
cgagatcctc gccgtcgggc atgcgcgcct tgagcctggc gaacagttcg gctggcgcga   2940
gccCctgatg ctcttcgtcc agatcatctg atcgacaaga cccggctcca tcccgagtac   3000
gtgctcgctc gatgcgatgt ttcgcttggt ggtcgaatgg gcaggtagcc ggatcaagcg   3060
tatgcagccg ccgcattgca tcagccatga tggatactTT ctcggcagga gcaaggtgag   3120
atgacaggag atcctgcccc ggcacttcgc ccaatagcag ccagtccctt cccgcttcag   3180
tgacaacgtc gagcacagct gcgcaaggaa cgcccgtcgt ggccagccac gatagccgcg   3240
ctgcctcgtc ctgcagttca ttcagggcac cggacaggtc ggtcttgaca aaaagaaccg   3300
ggcgcccctg cgctgacagc cggaacacgg cggcatcaga gcagccgatt gtctgttgtg   3360
cccagtcata gccgaatagc ctctccaccc aagcggccgg agaacctgcg tgcaatccat   3420
cttgttcaat catgcgaaac gatcctcatc ctgtctcttg atcagatctt gatccctgc    3480 gccatcagat ccttggcggc aagaaagcca tccagtttac tttgcagggc ttcccaacct   3540
taccagaggg cgccccagct ggcaattccg gttcgcttgc tgtccataaa accgccagt    3600 ctagctatcg ccatcccggg accttctagt agatctgaat tcggtgaggt tatggcggag   3660
ggttgcgagg tctaggagaa cagaggaagt catgctttga agcatataag ctgccctgcc   3720
cctcaaggtt ttcttcaagt gaggttttat ctaactgcct aacggcaggg gaaccgtata   3780
ttgcttacgg tatgagaccc cttaaacgtc cggatagtca ccgctcttct ttagctccgc   3840
gacatgccta gcaaccgtgg cgcgagagac tcctacctct gcccctattt cagcccacgt   3900
gggaactgtc cctgtctgga aatactgatc gttcaccatt tggctaatac gggacttcgt   3960
agatcgtcct tgagccttTT tcttacggtg cgtcttttca agcttcgacc tttgtgcttg   4020
cgcatatttg ccctcggggt ctgttTtcca gcgttgtgcg gcTTTTtgtc cgcctctgcg   4080
tcccatcgtg gccaaggctt tccgctcgct gctggtggct ttacctggtg cgttagagcc   4140
gctgtaggtc tcgctcttgg attgggcgac atacccgcgc acgcgccttg ccatggtttg   4200
gcggtcgcgc atgggtggca tctcgttgtc gcggcctgca ccgccgtggg tgtgtgcgac   4260
gttgtaggcg tgctcatagg cgtcgatgat tgctgcgtct gtcaggcgtt ggccttgctg   4320
gcgcaagcgg tggccagtct taagcgcatg tctaaaggct gtttcgtcgc gtgctgcggt   4380
tccttggaca atccagagca cacgcacacc gtcgataagt tccgggtcat actggtcgag   4440
accaccggcg atttccgcgt ctacgtcctg ggcgagtgct ttgaatgctt gggcttcttc   4500
acggcgggtc ttgaccgcgt tgataagttc gcggccagag ctgaattgct ggcgtggggt   4560
ggggttgaac tggtcgtgtc ctgccatatc ccttacctgc tttatcaagt ctccaaggcg   4620
catcacccgg ttgtgctgcc tataccaacg ataagcggta ggggctttgc ctgtgtagaa   4680
cggggttgcg ctaaagcggt gggaaaagtg cgggtcatgt tctaaaagct cacccagcac   4740
acgcgtggtt gctgcaagaa gcttcatctg cgcagattta ccgttacggt cagcgtagac   4800
agggtcaata agccatatga actgggcttt gccgttagtt gggttaatac ccacccaggc   4860
tggcccgacg ctatgagtaa tcagtgagcg caccacgtcg cggacgtacg ggtttaagtc   4920
```

```
tgcggggtca ccgcctgcgg tacctacttg gtcaacgtct acgaccagga cggcggcgta    4980
ctgcttggtg gtgagcatgg cgtactcgca ccgtcctaaa gcatcagtct cgaagcgata    5040
catacgcggc gagttcgtgc cgtcagcgtt gcgtcgatag gccttttaa agtctcgtgt     5100 gactgaaccg tggagtacat cgcggcctag atgatcgcgt aaaaggtcgc ggtcactggc    5160
agatgctggg gtgttgtcca gtccaccacg gtcgcgctcg acgcgggtag gtgttttagt    5220
gtgcgcattc tgcgcatgag tctgtaaact catgaccgtg atttctccca ggtgtgtgct    5280
gggtgataag cgaaagtcat cgggttgccg cccggtggct ttcttcgttt ttcattgtct    5340
ttccctgact ctaaatgaca ccggtgttat ttactagcca tgacacgcga aaaatatgcc    5400
ttttacctgc ggttacgtat ggctagacat atggcaagct atacgtaacc gcgtttcagc    5460
tgcacagggc tgtctgcgca gatttaccat agatctacta g                       5501
```

```
<210> SEQ ID NO 16
<211> LENGTH: 39
<212> TYPE: DNA
<213> ORGANISM: Artificial Sequence
<220> FEATURE:
<223> OTHER INFORMATION: Synthetic primer

<400> SEQUENCE: 16
gcgcggacta gtagatctat ggtaaatctg cgcagacag                            39

<210> SEQ ID NO 17
<211> LENGTH: 33
<212> TYPE: DNA
<213> ORGANISM: Artificial Sequence
<220> FEATURE:
<223> OTHER INFORMATION: Synthetic primer

<400> SEQUENCE: 17
gcgcggacta gtgaattcgg tgaggttatg gcg                                  33

<210> SEQ ID NO 18
<211> LENGTH: 35
<212> TYPE: DNA
<213> ORGANISM: Artificial Sequence
<220> FEATURE:
<223> OTHER INFORMATION: Synthetic primer

<400> SEQUENCE: 18
aaggtcccgg gatggcgata gctagactgg gcggt                                35

<210> SEQ ID NO 19
<211> LENGTH: 32
<212> TYPE: DNA
<213> ORGANISM: Artificial Sequence
<220> FEATURE:
<223> OTHER INFORMATION: Synthetic primer

<400> SEQUENCE: 19
aaggtcccgg gggttgggcg tcgcttggtc gg                                   32

<210> SEQ ID NO 20
<211> LENGTH: 37
<212> TYPE: DNA
<213> ORGANISM: Artificial Sequence
<220> FEATURE:
<223> OTHER INFORMATION: Synthetic primer

<400> SEQUENCE: 20
ggagcactag tctgaaatga gctgttgaca attaatc                              37
```

<210> SEQ ID NO 21
<211> LENGTH: 39
<212> TYPE: DNA
<213> ORGANISM: Artificial Sequence
<220> FEATURE:
<223> OTHER INFORMATION: Synthetic primer

<400> SEQUENCE: 21
ggagcactag ttttaaacat gagcggatac atatttgaa           39

<210> SEQ ID NO 22
<211> LENGTH: 36
<212> TYPE: DNA
<213> ORGANISM: Artificial Sequence
<220> FEATURE:
<223> OTHER INFORMATION: Synthetic primer

<400> SEQUENCE: 22
atgaataaga aaaaaatgat tttaacaagt ctagcc              36

<210> SEQ ID NO 23
<211> LENGTH: 62
<212> TYPE: DNA
<213> ORGANISM: Artificial Sequence
<220> FEATURE:
<223> OTHER INFORMATION: Synthetic primer

<400> SEQUENCE: 23
cgagagagat ctaaattaaa atgtcaaatg ttcttaacat gctttaattt ttattttggt    60
gc                                                                  62

<210> SEQ ID NO 24
<211> LENGTH: 47
<212> TYPE: DNA
<213> ORGANISM: Artificial Sequence
<220> FEATURE:
<223> OTHER INFORMATION: Synthetic primer

<400> SEQUENCE: 24
gagcgatgga tcctagaaag gtgtgtttca cccatgaata agaaaaa    47

<210> SEQ ID NO 25
<211> LENGTH: 48
<212> TYPE: DNA
<213> ORGANISM: Artificial Sequence
<220> FEATURE:
<223> OTHER INFORMATION: Synthetic primer

<400> SEQUENCE: 25
tcaaatgttc ttaacatgct ttaattttta tggtgcagga gctggttg    48

<210> SEQ ID NO 26
<211> LENGTH: 45
<212> TYPE: DNA
<213> ORGANISM: Artificial Sequence
<220> FEATURE:
<223> OTHER INFORMATION: Synthetic primer

<400> SEQUENCE: 26
atgttaagaa catttgacat tttaatttcg gcactggccg tcgtt       45

<210> SEQ ID NO 27
<211> LENGTH: 27
<212> TYPE: DNA

```
<213> ORGANISM: Artificial Sequence
<220> FEATURE:
<223> OTHER INFORMATION: Synthetic primer

<400> SEQUENCE: 27
gcgatatgga tcccatgagc ggataca                                        27

<210> SEQ ID NO 28
<211> LENGTH: 377
<212> TYPE: PRT
<213> ORGANISM: Streptococcus pneumoniae

<400> SEQUENCE: 28
```

| | | | | | | | | | | | | | | |
|---|---|---|---|---|---|---|---|---|---|---|---|---|---|---|
| Ala | Ser | Ser | Pro | Thr | Val | Val | Arg | Ala | Glu | Asp | Ala | Pro | Val | Ala | Asn |
| 1 | | | | 5 | | | | | 10 | | | | | 15 | |
| Gln | Ser | Lys | Ala | Glu | Lys | Asp | Tyr | Asp | Ala | Ala | Lys | Arg | Asp | Ala | Glu |
| | | | 20 | | | | | 25 | | | | | 30 | | |
| Asn | Ala | Lys | Lys | Ala | Leu | Glu | Asp | Ala | Lys | Arg | Ala | Gln | Lys | Lys | Tyr |
| | | 35 | | | | | 40 | | | | | 45 | | | |
| Lys | Asp | Asp | Gln | Lys | Ile | Thr | Glu | Glu | Lys | Ala | Glu | Glu | Lys | Lys |
| 50 | | | | | 55 | | | | | 60 | | | | |
| Ala | Ser | Gln | Glu | Gln | Lys | Ala | Asn | Leu | Asp | Tyr | Gln | Lys | Leu |
| 65 | | | | 70 | | | | | 75 | | | | 80 |
| Arg | Lys | Tyr | Ile | Asn | Glu | Lys | Asp | Ser | Lys | Lys | Arg | Ser | Met | Leu | Gln |
| | | | | 85 | | | | | 90 | | | | | 95 | |
| Lys | Glu | Met | Glu | Glu | Ala | Glu | Arg | Lys | Asp | Lys | Glu | Lys | Gln | Ala | Glu |
| | | | 100 | | | | | 105 | | | | | 110 | | |
| Phe | Lys | Lys | Ile | Arg | Glu | Lys | Val | Ile | Pro | Ser | Ala | Glu | Glu | Leu | Thr |
| | | 115 | | | | | 120 | | | | | 125 | | | |
| Glu | Thr | Arg | Arg | Lys | Ala | Glu | Glu | Ala | Glu | Ala | Lys | Glu | Pro | Glu | Leu |
| 130 | | | | | 135 | | | | | 140 | | | | | |
| Thr | Lys | Lys | Val | Lys | Glu | Ala | Glu | Glu | Lys | Val | Thr | Glu | Ala | Lys | Gln |
| 145 | | | | | 150 | | | | | 155 | | | | | 160 |
| Lys | Leu | Asp | Ala | Glu | Arg | Ala | Lys | Glu | Val | Ala | Leu | Gln | Ala | Lys | Ile |
| | | | | 165 | | | | | 170 | | | | | 175 | |
| Ala | Glu | Leu | Glu | Asn | Glu | Val | His | Arg | Leu | Glu | Thr | Lys | Leu | Lys | Glu |
| | | | 180 | | | | | 185 | | | | | 190 | | |
| Thr | Asp | Glu | Ser | Asp | Ser | Glu | Asp | Tyr | Val | Lys | Glu | Gly | Leu | Arg | Ala |
| | | 195 | | | | | 200 | | | | | 205 | | | |
| Pro | Leu | Gln | Ser | Glu | Leu | Asp | Ala | Lys | Gln | Ala | Lys | Leu | Ser | Lys | Leu |
| 210 | | | | | 215 | | | | | 220 | | | | | |
| Glu | Glu | Leu | Ser | Asp | Lys | Ile | Asp | Glu | Leu | Asp | Ala | Glu | Ile | Ala | Lys |
| 225 | | | | | 230 | | | | | 235 | | | | | 240 |
| Leu | Glu | Lys | Asp | Val | Glu | Asp | Phe | Lys | Asn | Ser | Asp | Gly | Glu | Tyr | Ser |
| | | | | 245 | | | | | 250 | | | | | 255 | |
| Ala | Leu | Tyr | Leu | Glu | Ala | Ala | Glu | Lys | Asp | Leu | Ala | Ala | Lys | Lys | Ala |
| | | | 260 | | | | | 265 | | | | | 270 | | |
| Glu | Leu | Glu | Lys | Thr | Glu | Ala | Asp | Leu | Lys | Lys | Ala | Val | Asn | Glu | Pro |
| | | 275 | | | | | 280 | | | | | 285 | | | |
| Glu | Lys | Pro | Ala | Pro | Ala | Pro | Glu | Thr | Pro | Ala | Pro | Glu | Ala | Pro | Ala |
| 290 | | | | | 295 | | | | | 300 | | | | | |
| Glu | Gln | Pro | Lys | Pro | Ala | Pro | Ala | Pro | Gln | Pro | Ala | Pro | Ala | Pro | Lys |
| 305 | | | | | 310 | | | | | 315 | | | | | 320 |
| Pro | Glu | Lys | Pro | Ala | Glu | Gln | Pro | Lys | Pro | Glu | Lys | Thr | Asp | Asp | Gln |
| | | | | 325 | | | | | 330 | | | | | 335 | |

```
Gln Ala Glu Glu Asp Tyr Ala Arg Arg Ser Glu Glu Tyr Asn Arg
                340                 345                 350

Leu Thr Gln Gln Gln Pro Pro Lys Ala Glu Lys Pro Ala Pro Ala Pro
            355                 360                 365

Lys Pro Glu Gln Pro Ala Pro Gly Thr
    370                 375

<210> SEQ ID NO 29
<211> LENGTH: 400
<212> TYPE: PRT
<213> ORGANISM: Streptococcus pneumoniae

<400> SEQUENCE: 29

Met Asn Lys Lys Lys Met Ile Leu Thr Ser Leu Ala Ser Val Ala Ile
1               5                   10                  15

Leu Gly Ala Gly Phe Val Thr Ser Gln Pro Thr Phe Val Arg Ala Glu
            20                  25                  30

Glu Ala Pro Val Ala Asn Gln Ser Lys Ala Glu Lys Asp Tyr Asp Ala
        35                  40                  45

Ala Lys Arg Asp Ala Glu Asn Ala Lys Lys Ala Leu Glu Asp Ala Lys
    50                  55                  60

Arg Ala Gln Lys Lys Tyr Lys Asp Asp Gln Lys Ile Thr Glu Glu Lys
65                  70                  75                  80

Ala Glu Glu Lys Lys Ala Ser Gln Glu Gln Gln Lys Ala Asn Leu
                85                  90                  95

Asp Tyr Gln Gln Lys Leu Arg Lys Tyr Ile Asn Glu Lys Asp Ser Lys
                100                 105                 110

Lys Arg Ser Met Leu Gln Lys Glu Met Glu Glu Ala Glu Arg Lys Asp
            115                 120                 125

Lys Glu Lys Gln Ala Glu Phe Lys Lys Ile Arg Glu Lys Val Ile Pro
        130                 135                 140

Ser Ala Glu Glu Leu Thr Glu Thr Arg Arg Lys Ala Glu Glu Ala Glu
145                 150                 155                 160

Ala Lys Glu Pro Glu Leu Thr Lys Lys Val Lys Glu Ala Glu Lys
                165                 170                 175

Val Thr Glu Ala Lys Gln Lys Leu Asp Ala Glu Arg Ala Lys Glu Val
            180                 185                 190

Ala Leu Gln Ala Lys Ile Ala Glu Leu Glu Asn Glu Val His Arg Leu
        195                 200                 205

Glu Thr Lys Leu Lys Glu Ile Asp Glu Ser Asp Ser Glu Asp Tyr Val
    210                 215                 220

Lys Glu Gly Leu Arg Ala Pro Leu Gln Ser Glu Leu Asp Ala Lys Gln
225                 230                 235                 240

Ala Lys Leu Ser Lys Leu Glu Glu Leu Ser Asp Lys Ile Asp Glu Leu
                245                 250                 255

Asp Ala Glu Ile Ala Lys Leu Glu Lys Asp Val Glu Asp Phe Lys Asn
            260                 265                 270

Ser Asp Gly Glu Tyr Ser Ala Leu Tyr Leu Glu Ala Ala Glu Lys Asp
        275                 280                 285

Leu Ala Ala Lys Lys Ala Glu Leu Glu Lys Thr Glu Ala Asp Leu Lys
    290                 295                 300

Lys Ala Val Asn Glu Pro Glu Lys Pro Ala Pro Ala Pro Glu Thr Pro
305                 310                 315                 320

Ala Pro Glu Ala Pro Ala Glu Gln Pro Lys Pro Ala Pro Ala Pro Gln
                325                 330                 335
```

-continued

```
Pro Ala Pro Ala Pro Lys Pro Glu Lys Pro Ala Glu Gln Pro Lys Pro
            340             345             350
Glu Lys Thr Asp Asp Gln Gln Ala Glu Glu Asp Tyr Ala Arg Arg Ser
            355             360             365
Glu Glu Glu Tyr Asn Arg Leu Thr Gln Gln Gln Pro Pro Lys Ala Glu
    370             375             380
Lys Pro Ala Pro Ala Pro Lys Pro Glu Gln Pro Ala Pro Ala Pro Lys
385             390             395             400
```